United States Patent
Diebolt et al.

(10) Patent No.: US 9,795,952 B2
(45) Date of Patent: Oct. 24, 2017

(54) BIDENTATE LIGANDS FOR HYDROFORMYLATION OF ETHYLENE

(71) Applicant: Dow Technology Investments LLC, Midland, MI (US)

(72) Inventors: Olivier Diebolt, Tarragona (ES); Hugo Tricas, Tarragona (ES); Pertrus W. N. M. van Leeuwen, Kockengen (NL); Heather Anne Spinney, Midland, MI (US); Robert David John Froese, Midland, MI (US); Michael A. Brammer, Lake Jackson, TX (US)

(73) Assignee: Dow Technology Investments LLC, Midland, MI (US)

( * ) Notice: Subject to any disclaimer, the term of this patent is extended or adjusted under 35 U.S.C. 154(b) by 53 days.

(21) Appl. No.: 14/648,803

(22) PCT Filed: Nov. 19, 2013

(86) PCT No.: PCT/US2013/070753
§ 371 (c)(1),
(2) Date: Jun. 1, 2015

(87) PCT Pub. No.: WO2014/088800
PCT Pub. Date: Jun. 12, 2014

(65) Prior Publication Data
US 2015/0328628 A1    Nov. 19, 2015

(30) Foreign Application Priority Data

Dec. 4, 2012  (EP) ..................... 12382481

(51) Int. Cl.
*B01J 31/18* (2006.01)
*C07C 45/50* (2006.01)
(52) U.S. Cl.
CPC ........... *B01J 31/186* (2013.01); *B01J 31/187* (2013.01); *C07C 45/50* (2013.01);
(Continued)
(58) Field of Classification Search
CPC .. B01J 31/186; B01J 31/187; B01J 2231/321; B01J 2531/822; C07C 45/50
(Continued)

(56) References Cited

U.S. PATENT DOCUMENTS 3,527,809 A   9/1970 Pruett et al.
4,148,830 A   4/1979 Pruett et al.
(Continued)

FOREIGN PATENT DOCUMENTS

CN   1857776 A   11/2006
CN   102746338 A  10/2012
(Continued)

OTHER PUBLICATIONS

English abstract of JP 2002-47294 published on Feb. 12, 2002.*
(Continued)

*Primary Examiner* — Kristin Vajda
(74) *Attorney, Agent, or Firm* — Husch Blackwell LLP

(57) ABSTRACT

A process for the hydroformylation of ethylene, with a transition metal, e.g., rhodium, catalyst promoted with a bidentate ligand of Formula I, II or III in which each $R_1$-$R_{24}$ are independently a hydrogen, a hydrocarbyl group, an aromatic ring, a heteroaromatic ring or a halogen atom, or a heterocarbyl group. $X_1$ is $CH_2$ or O, while $X_2$ is O or $C(R_{25})_2$, where each $R_{25}$ may be the same or different and is a hydrogen, a cycloaliphatic group, an aromatic ring, a heteroaromatic ring or a halogen atom, or a heterocarbyl group, wherein two $R_{25}$ groups may combine in a fused ring, and Y is a pyrrole group bound via the nitrogen atom to phosphorus, wherein each pyrrole group may bear multiple substituents selected from among the groups alkyl, alkoxy, acyl, carboxyl, carboxylate, cyano, —$SO_3H$, sulfonate, amino, trifluoromethyl and halogen.

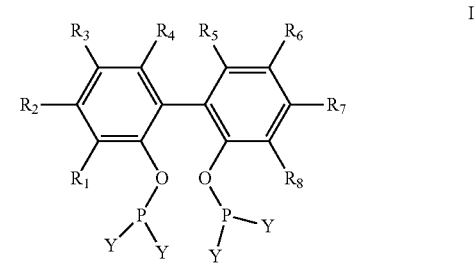

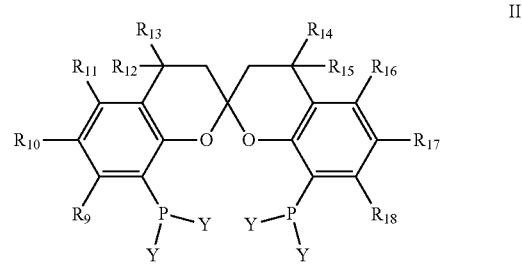

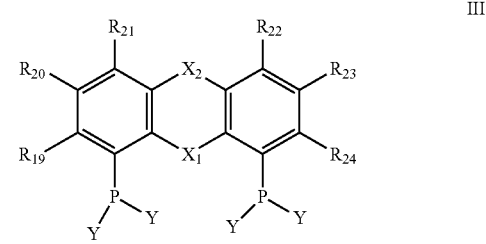

8 Claims, No Drawings

(52) U.S. Cl.
CPC .... *B01J 2231/321* (2013.01); *B01J 2531/822* (2013.01); *Y02P 20/582* (2015.11)

(58) Field of Classification Search
USPC .................................................. 548/402, 400
See application file for complete search history.

(56) References Cited

U.S. PATENT DOCUMENTS

| | | | |
|---|---|---|---|
| 4,247,486 | A | 1/1981 | Brewester et al. |
| 4,668,651 | A | 5/1987 | Billig et al. |
| 4,774,361 | A | 9/1988 | Maher et al. |
| 5,102,505 | A | 4/1992 | Sorensen |
| 5,110,990 | A | 5/1992 | Blessing et al. |
| 5,288,918 | A | 2/1994 | Maher et al. |
| 5,312,996 | A | 5/1994 | Packett |
| 5,430,194 | A | 7/1995 | Barner et al. |
| 5,681,473 | A | 10/1997 | Miller et al. |
| 5,710,344 | A | 1/1998 | Breikss et al. |
| 5,929,289 | A | 7/1999 | Abatjoglou et al. |
| 7,173,138 | B2 | 2/2007 | Ahlers et al. |
| 2004/0110960 | A1 | 6/2004 | Ahlers et al. |
| 2011/0269997 | A1 | 11/2011 | Cox et al. |
| 2012/0259142 | A1 | 10/2012 | Eisenschmid et al. |

FOREIGN PATENT DOCUMENTS

| | | |
|---|---|---|
| JP | 2002-47294 A | 2/2002 |
| JP | 2002047294 A | 2/2002 |
| WO | 88/08835 A1 | 11/1988 |
| WO | 99/52632 A1 | 10/1999 |
| WO | 03/018192 A2 | 3/2003 |
| WO | 2005/009934 A2 | 2/2005 |
| WO | 2005/120705 A1 | 12/2005 |

OTHER PUBLICATIONS

Diebolt et al., Adv. Synth. Catal. 2012, 354, 670-677.
Boymans et al., Dalton Trans., 2013, 42, 137-142.
Van der Slot, et al., Organometallics 2002, vol. 21, No. 19, 3873-3883.
Huang, et al., Organometallics, 1997, vol. 16, pp. 3377-3380.

* cited by examiner

BIDENTATE LIGANDS FOR HYDROFORMYLATION OF ETHYLENE

FIELD OF THE INVENTION

This invention relates to the hydroformylation of ethylene. In one aspect the invention relates to the hydroformylation of ethylene with a rhodium metal promoted catalyst while in another aspect, the invention relates to the use of a bidentate ligand to promote the rhodium metal catalyst.

BACKGROUND OF THE INVENTION

For industrial ethylene hydroformylation processes, the catalyst of choice typically comprises rhodium metal promoted with triphenylphosphine (TPP). Rhodium-TPP is a proven, dependable technology capable of delivering excellent production rates, but maintaining these high rates throughout the lifetime of the catalyst requires high reaction temperatures. In hydroformylation processes, high temperature promotes aldol condensation, and this in turn lowers olefin efficiency and produces high boiling by-products. The ever increasing reactor volume taken up by these "heavies" can ultimately limit the effective life of the catalyst. Maintaining production rates in a rhodium-TPP process also requires relatively large amounts of rhodium, which may add significantly to the overall cost of the process. Thus a catalyst capable of maintaining high production rates at lower temperatures and/or with less rhodium would improve process economics.

The activity of a rhodium-catalyzed hydroformylation process is determined to a large extent by the ligand employed, but it is also dependent on the olefin substrate. For example, it is well known that terminal olefins are much more reactive than internal olefins. While most rhodium-ligand combinations will demonstrate reasonable reaction rates for ethylene hydroformylation, the absolute reaction rate of a given catalyst is not readily predicted based on results obtained with other olefins. For example, many rhodium-ligand combinations that give very high reaction rates for propylene hydroformylation are only moderately active for ethylene hydroformylation. The reason for these observed relative differences is not understood, however the fact remains that the activity of a rhodium catalyst promoted by a particular ligand for the hydroformylation of other olefins is not predictive for the hydroformylation of ethylene.

SUMMARY OF THE INVENTION

In one embodiment the invention is a process for the hydroformylation of ethylene, with a transition metal, e.g., rhodium, catalyst promoted with a bidentate ligand of Formula I, II or III:

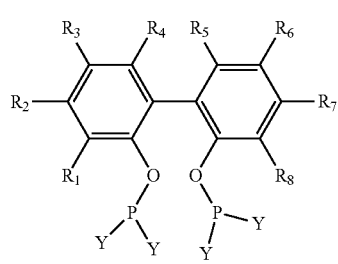

Formula I

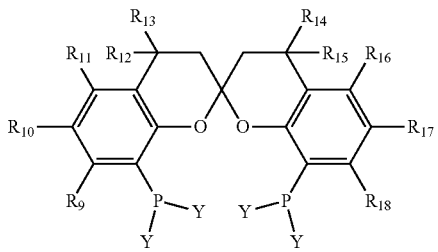

Formula II

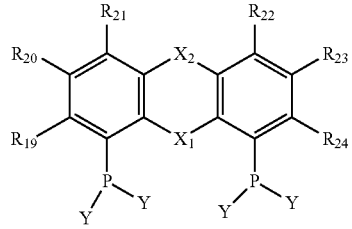

Formula III in which each $R_1$-$R_{24}$ are independently a hydrogen, a hydrocarbyl group, an aromatic ring, a heteroaromatic ring or a halogen atom, or a heterocarbyl group selected from the groups consisting of $NR_2$, OR and SR, where R is a hydrocarbyl group of $C_1$ to $C_{20}$, or heterohydrocarbyl group having 1 to 20 atoms, each independently selected from C or a heteroatom, wherein each heteroatom is independently O, S, Si, Ge, P, or N, and may themselves be substituted or unsubstituted as required by the valency of the heteroatom. $R_1$ to $R_{24}$ may optionally comprise cycloaliphatic or aryl groups fused to the biaryl moiety such as:

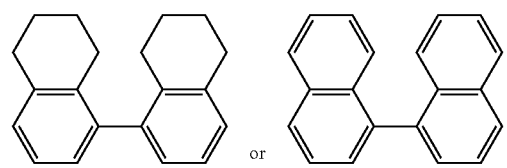

for Formula I, II, or III, each aryl, heteroaryl, hydrocarbyl, heterohydrocarbyl, hydrocarbylene, and heterohydrocarbylene group independently is unsubstituted or substituted with one or more substituents $R^v$. Each $R^v$ independently is a halogen atom, polyfluoroalkyl substitution, unsubstituted $C_1$ to $C_{18}$ alkyl, $F_3C$—, $FCH_2O$—, $F_2HCO$—, $F_3CO$—, $R_3Si$, $R_3Ge$, RO, RS, RS(O), $RS(O)_2$, $R_2P$, $R_2N$, $R_2C$=N, NC, RC(O)O, ROC(O), RC(O)N(R), or $R_2NC(O)$, or two of the $R^v$ are taken together to form an un unsubstituted $C_1$ to $C_{18}$ alkylene, wherein each R independently is an unsubstituted $C_1$ to $C_{18}$ alkyl. Optionally, two of the $R^v$ are taken together to form a ring, where the ring can be cyclic or polycyclic.

$X_1$ is $CH_2$ or O, while $X_2$ is O or $C(R_{25})_2$, and each $R_{25}$ may be the same or different and is a hydrogen, a cycloaliphatic group, an aromatic ring, a heteroaromatic ring or a halogen atom, or a heterocarbyl group selected from the groups consisting of $NR_2$, OR and SR, where R is a hydrocarbyl group of $C_1$ to $C_{20}$, or heterohydrocarbyl group having 1 to 20 atoms, each independently selected from C or a heteroatom, wherein each heteroatom is independently O, S, Si, Ge, P, or N, and may themselves be substituted or unsubstituted as required by the valency of the heteroatom. Two $R_{25}$ groups may combine in a fused ring. Y is a pyrrole group bound via the nitrogen atom to phosphorus.

For the purposes of the present invention, the expression "pyrrole group" refers to a series of unsubstituted or substituted heteroaromatic groups which are structurally derived from the pyrrole skeleton and whose heterocycle contains a pyrrolic nitrogen atom. The expression "pyrrole group" thus encompasses the unsubstituted or substituted groups pyrrolyl, indolyl, imidazolyl, pyrazolyl, purinyl, indazolyl, benzotriazolyl, 1,2,3-triazolyl, 1,3,4-triazolyl and carbazolyl. The "pyrrole group" may bear multiple substituents selected from among the groups alkyl, alkoxy, acyl, carboxyl, carboxylate, cyano, —$SO_3H$, sulfonate, amino, trifluoromethyl and halogen.

The bidentate ligand promoted transition metal catalysts of this invention, particularly rhodium-based catalysts, exhibit unprecedented activity for the hydroformylation of ethylene, in some cases about 100 times the reactivity of rhodium catalysts promoted with TPP. This, in turn, allows for increased production rates at lower temperatures and rhodium concentrations.

DETAILED DESCRIPTION OF THE PREFERRED EMBODIMENT

Definitions

Unless stated to the contrary, implicit from the context, or customary in the art, all parts and percents are based on weight. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

All references to the Periodic Table of the Elements and the various groups therein are to the version published in the CRC Handbook of Chemistry and Physics, 72nd Ed. (1991-1992) CRC Press, at page I-10.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, etc., is from 100 to 1,000, then all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the amount of catalyst to use in the hydroformylation process "Hydroformylation" and like terms include, but not limited to, all permissible asymmetric and non-asymmetric hydroformylation processes that involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes.

"Substituted" and like terms include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxyalkyl, aminoalkyl, in which the number of carbons can range from 1 to 20 or more, preferably from 1 to 12, as well as hydroxy, halo, and amino. The permissible substituents can be one or more and the same or different for appropriate organic compounds. This invention is not intended to be limited in any manner by the permissible substituents of organic compounds.

The terms "reaction fluid," "reaction medium" and "catalyst solution" are used interchangeably, and may include, but are not limited to, a mixture comprising: (a) a metal-bidentate ligand complex catalyst, (b) free bidentate ligand, (c) aldehyde product formed in the reaction, (d) unreacted reactants, (e) a solvent for said metal-bidentate ligand complex catalyst and said free bidentate ligand, and, optionally, (f) one or more ligand degradation products formed in the reaction (which may be homogeneous or heterogeneous, and these compounds include those adhered to process equipment surfaces). The reaction fluid can encompass, but is not limited to, (a) a fluid in a reaction zone, (b) a fluid stream on its way to a separation zone, (c) a fluid in a separation zone, (d) a recycle stream, (e) a fluid withdrawn from a reaction zone or separation zone, (f) a fluid returned to a reaction zone or separation zone, (h) a fluid in an external cooler, and (i) ligand decomposition products and the like.

"Comprising", "including", "having" and like terms are not intended to exclude the presence of any additional component, step or procedure, whether or not the same is specifically disclosed. In order to avoid any doubt, all processes claimed through use of the term "comprising" may include one or more additional steps, pieces of equipment or component parts, and/or materials unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or", unless stated otherwise, refers to the listed members individually as well as in any combination.

Syngas

Hydrogen and carbon monoxide may be obtained from any suitable source, including petroleum cracking and refinery operations. Syngas mixtures are a preferred source of hydrogen and CO. Syngas (from synthesis gas) is the name given to a gas mixture that contains varying amounts of CO and $H_2$. Production methods for it are well known. Hydrogen and CO typically are the main components of syngas, but syngas may contain carbon dioxide ($CO_2$) and inert gases such as nitrogen ($N_2$) and argon (Ar). The ratio of $H_2$ to CO varies greatly but generally ranges from 1:100 to 100:1 and preferably between 1:10 and 10:1. Syngas is commercially available and is often used as a fuel source or as an intermediate for the production of other chemicals. The most preferred $H_2$:CO ratio for chemical production is between 3:1 and 1:3 and usually is targeted to be between about 1:2 and 2:1 for most hydroformylation applications.

Solvent

A solvent is typically and advantageously employed in the hydroformylation process of this invention. Any suitable solvent that does not unduly interfere with the hydroformylation process can be used. By way of illustration, suitable solvents for rhodium catalyzed hydroformylation processes include those disclosed, for example, in U.S. Pat. Nos. 3,527,809; 4,148,830; 5,312,996; and 5,929,289. Non-limiting examples of suitable solvents include saturated hydrocarbons (alkanes), aromatic hydrocarbons, water, ethers, aldehydes, ketones, nitriles, alcohols, esters, and aldehyde condensation products. Specific examples of solvents include: tetraglyme, pentanes, cyclohexane, heptanes, benzene, xylene, toluene, diethyl ether, tetrahydrofuran, butyraldehyde, and benzonitrile. The organic solvent may also contain dissolved water up to the saturation limit. Illustrative preferred solvents include ketones (e.g. acetone and methylethyl ketone), esters (e.g. ethyl acetate, di-2-ethylhexyl phthalate, 2,2,4-trimethyl-1,3-pentanediol monoisobutyrate), hydrocarbons (e.g. toluene), nitro-hydrocarbons (e.g. nitrobenzene), ethers (e.g. tetrahydrofuran (THF)) and sulfolane.

In rhodium-catalyzed hydroformylation processes, it may be preferred to employ, as a primary solvent, aldehyde compounds corresponding to the aldehyde products desired to be produced and/or higher boiling aldehyde liquid condensation by-products, for example, as might be produced in situ during the hydroformylation process, as described for example in U.S. Pat. Nos. 4,148,380 and 4,247,486. The primary solvent will normally eventually comprise both aldehyde products and higher boiling aldehyde liquid condensation by-products ("heavies"), due to the nature of the continuous process. The amount of solvent is not especially critical and need only be sufficient to provide the reaction medium with the desired amount of transition metal concentration. Typically, the amount of solvent ranges from about 5 percent to about 95 percent by weight, based on the total weight of the reaction fluid. Mixtures of solvents may be employed.

Catalyst

Metal Component

The metal component of the catalysts used in the practice of this invention include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. Mixtures of these metals can be used.

Ligands

The organophosphorous compounds that may serve as the ligands of the catalysts used in the practice of this invention are bidentate ligands of Formulae I, II and III:

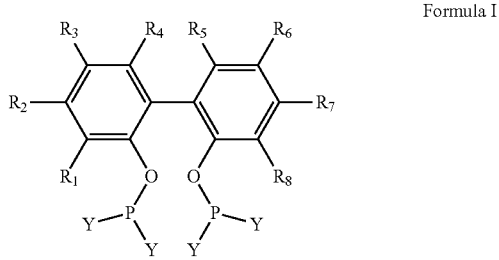

Formula I

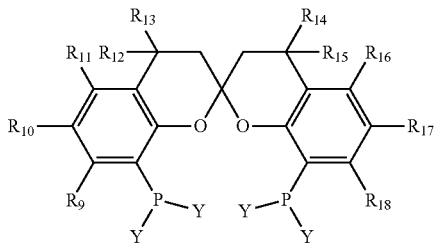

Formula II

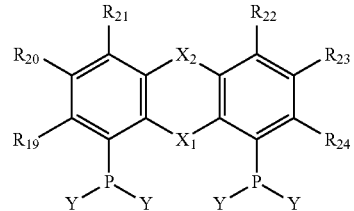

Formula III in which each $R_1$-$R_{24}$ are independently a hydrogen, a hydrocarbyl group, an aromatic ring, a heteroaromatic ring or a halogen atom, or a heterocarbyl group selected from the groups consisting of $NR_2$, OR and SR, where R is a hydrocarbyl group of $C_1$ to $C_{20}$, or heterohydrocarbyl group having 1 to 20 atoms, each independently selected from C or a heteroatom, wherein each heteroatom is independently O, S, Si, Ge, P, or N, and may themselves be substituted or unsubstituted as required by the valency of the heteroatom. $R_1$ to $R_{24}$ may optionally comprise cycloaliphatic or aryl groups fused to the biaryl moiety such as:

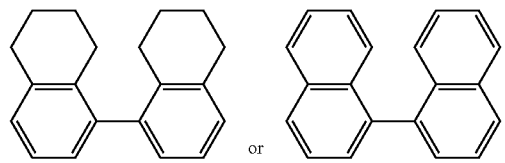

or for Formula I, II, or III, each aryl, heteroaryl, hydrocarbyl, heterohydrocarbyl, hydrocarbylene, and heterohydrocarbylene group independently is unsubstituted or substituted with one or more substituents $R^v$. Each $R^v$ independently is a halogen atom, polyfluoroalkyl substitution, unsubstituted $C_1$ to $C_{18}$ alkyl, $F_3C$—, $FCH_2O$—, $F_2HCO$—, $F_3CO$—, $R_3Si$, $R_3Ge$, RO, RS, RS(O), $RS(O)_2$, $R_2P$, $R_2N$, $R_2C=N$, NC, RC(O)O, ROC(O), RC(O)N(R), or $R_2NC(O)$, or two of the $R^v$ are taken together to form an un unsubstituted $C_1$ to $C_{18}$ alkylene, wherein each R independently is an unsubstituted $C_1$ to $C_{18}$ alkyl. Optionally, two of the $R^v$ are taken together to form a ring, where the ring can be cyclic or polycyclic.

$X_1$ is $CH_2$ or O, while $X_2$ is O or $C(R_{25})_2$, and each $R_{25}$ may be the same or different and is a hydrogen, a cycloaliphatic group, an aromatic ring, a heteroaromatic ring or a halogen atom, or a heterocarbyl group selected from the groups consisting of $NR_2$, OR and SR, where R is a hydrocarbyl group of $C_1$ to $C_{20}$, or heterohydrocarbyl group having 1 to 20 atoms, each independently selected from C or a heteroatom, wherein each heteroatom is independently O, S, Si, Ge, P, or N, and may themselves be substituted or unsubstituted as required by the valency of the heteroatom. Two $R_{25}$ groups may combine in a fused ring. Y is a pyrrole group bound via the nitrogen atom to phosphorus which may bear multiple substituents selected from among the groups alkyl, alkoxy, acyl, carboxyl, carboxylate, cyano, —$SO_3H$, sulfonate, amino, trifluoromethyl and halogen. Specific illustrative examples include the following structures:

Ligand 1
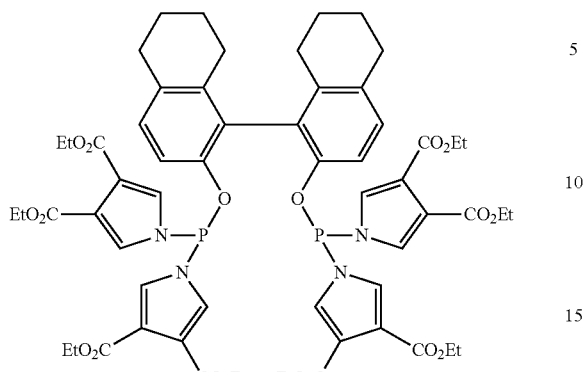
Ligand 2
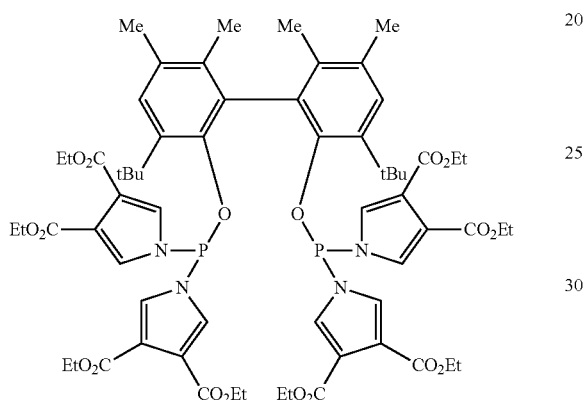
Ligand 3
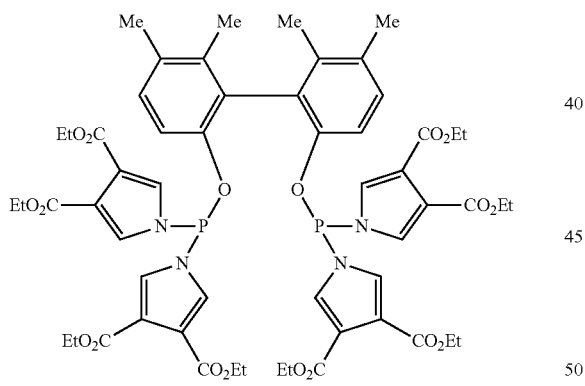
Ligand 4
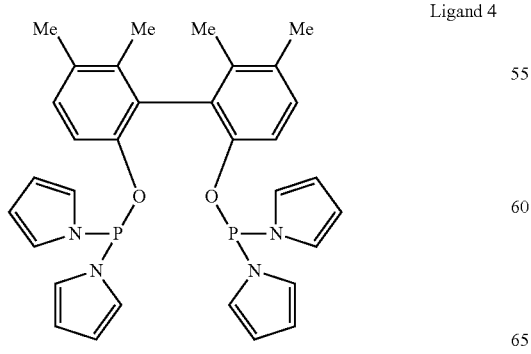
Ligand 5
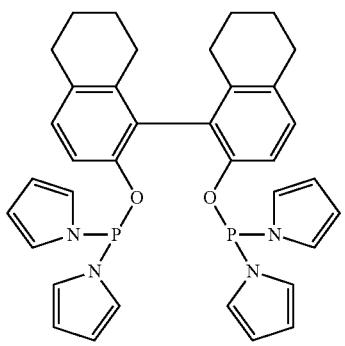
Ligand 6
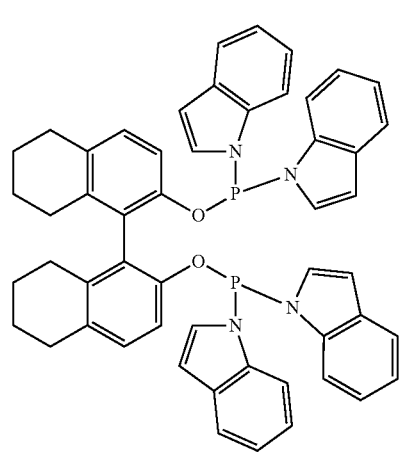
Ligand 7
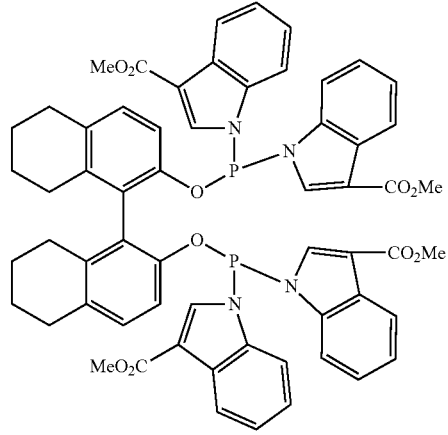

Ligand 8
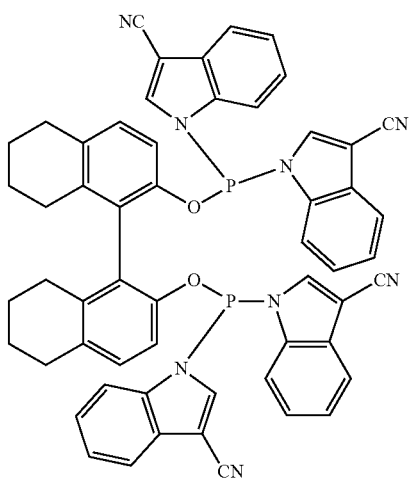

Ligand 9
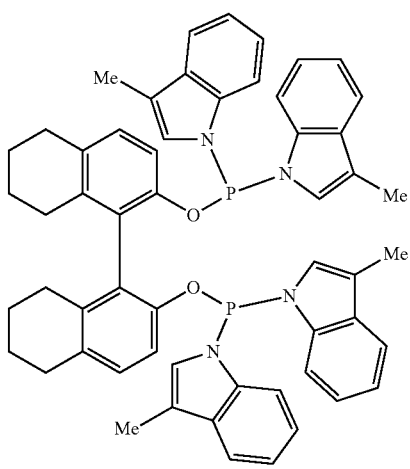

Ligand 10
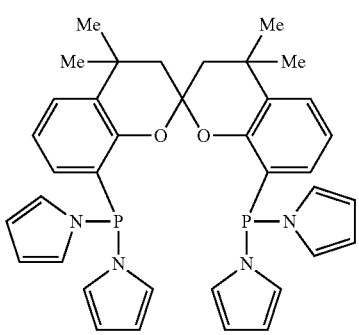

Ligand 11
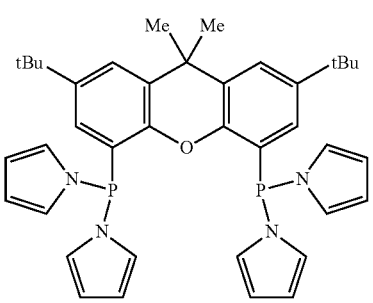

The ligand can be complexed with the metal and/or free in the reaction mixture.

Metal-Ligand Complex

The bidentate ligands that make up the metal-ligand complex and free bidentate ligand may be the same or different. These catalysts are prepared by methods known in the art for preparing organophosphorous compounds generally, including those methods disclosed in the patents mentioned above. In general, these catalysts may be pre-formed or formed in situ and comprise metal in complex combination with the bidentate ligand, carbon monoxide and, optionally, hydrogen. The ligand complex species may be present in mononuclear, dinuclear and/or higher nuclearity forms. However, the exact structure of the catalyst is not known.

The metal-bidentate ligand complex catalysts may be in homogeneous or heterogeneous form. For instance, preformed rhodium bidentate ligand catalysts may be prepared and introduced into a hydroformylation reaction mixture. More preferably, the rhodium-bidentate ligand complex catalysts can be derived from a rhodium catalyst precursor that may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, and $Rh(NO_3)_3$ may be introduced into the reaction mixture along with the bidentate ligand for the in situ formation of the active catalyst. In a preferred embodiment, rhodium dicarbonyl acetylacetonate is employed as a rhodium precursor and reacted in the presence of a solvent with the bidentate ligand to form a catalytic rhodium-bidentate ligand complex precursor that is introduced into the reactor along with excess (free) bidentate ligand for the in situ formation of the active catalyst. In any event, it is sufficient that carbon monoxide, hydrogen and the bidentate ligand are all ligands that are capable of being complexed with the metal and that an active metal-bidentate ligand catalyst is present in the reaction mixture under the conditions used in the hydroformylation reaction. Carbonyl and bidentate ligands may be complexed to the rhodium either prior to or in situ during the hydroformylation process.

By way of illustration, a preferred catalyst precursor composition consists essentially of a solubilized rhodium carbonyl bidentate ligand complex precursor, a solvent and, optionally, free bidentate ligand. The preferred catalyst precursor composition can be prepared by forming a solution of rhodium dicarbonyl acetylacetonate, an organic solvent and a bidentate ligand. The bidentate ligand readily replaces one of the carbonyl ligands of the rhodium acetylacetonate complex precursor as witnessed by the evolution of carbon monoxide gas.

Accordingly, the metal-bidentate ligand complex catalyst advantageously comprise the metal complexed with carbon monoxide and a bidentate ligand, the ligand being bonded (complexed) to the metal in a chelated and/or non-chelated fashion.

Mixtures of catalysts can be employed. The amount of metal-bidentate ligand complex catalyst present in the reaction fluid need only be that minimum amount necessary to provide the given metal concentration desired to be employed and that will furnish the basis for at least the catalytic amount of metal necessary to catalyze the particular hydroformylation process involved such as disclosed, for example, in the above-mentioned patents. In general, catalytic metal, e.g., rhodium, concentrations in the range of from 10 part per million by weight (ppmw) to 500 ppmw, calculated as free metal in the reaction medium, should be sufficient for most processes, while it is generally preferred to employ from 10 to 250 ppmw of metal, and more preferably from 10 to 100 ppmw of metal.

In addition to the metal-bidentate ligand complex catalyst, free bidentate ligand (i.e., ligand that is not complexed with the metal) may also be present in the reaction medium. The free bidentate ligand may correspond to any of the above-defined bidentate ligands discussed above. It is preferred that the free bidentate ligand be the same as the bidentate ligand of the metal-bidentate ligand complex catalyst employed. However, such ligands need not be the same in any given process. The hydroformylation process of this invention may involve from 0.1 moles or less to 100 moles or higher of free bidentate ligand per mole of metal in the reaction medium. Preferably, the hydroformylation process is carried out in the presence of from 1 to 50 moles of bidentate ligand per mole of metal present in the reaction medium. More preferably from 1.1 to 4 moles of bidentate ligand are employed per mole of metal. Said amounts of bidentate ligand are the sum of both the amount of bidentate ligand that is bound (complexed) to the metal present and the amount of free bidentate ligand present. If desired, additional bidentate ligand can be supplied to the reaction medium of the hydroformylation process at any time and in any suitable manner, e.g. to maintain a predetermined level of free ligand in the reaction medium.

Accordingly, the hydroformylation processing techniques that are advantageously employed may correspond to any known processing techniques such as, for example, gas recycle, liquid recycle, and combinations thereof. Preferred hydroformylation processes are those involving catalyst liquid recycle.

Hydroformylation Process

The hydroformylation process, and conditions for its operation, are well known. It comprises contacting carbon monoxide (CO), hydrogen ($H_2$), and at least one olefinic compound under hydroformylation conditions sufficient to form at least one aldehyde product in the presence of a catalyst comprising, as components, a transition metal and an organophosphorous ligand. Optional process components include an amine and/or water. The hydroformylation processes may be conducted in any batch, continuous or semi-continuous fashion and may involve any catalyst liquid and/or gas recycle operation desired. The particular hydroformylation process for producing propionaldehyde from ethylene, as well as the reaction conditions and ingredients of the hydroformylation process, can vary to convenience.

The recycle procedure generally involves withdrawing a portion of the liquid reaction medium containing the catalyst and aldehyde product from the hydroformylation reactor, i.e., reaction zone, either continuously or intermittently, and recovering the aldehyde product there from by use of a composite membrane, such as disclosed in U.S. Pat. Nos. 5,430,194 and 5,681,473, or by the more conventional and preferred method of distilling it, i.e. vaporization separation, in one or more stages under normal, reduced or elevated pressure, as appropriate, in a separate distillation zone, the non-volatilized metal catalyst containing residue being recycled to the reaction zone as disclosed, for example, in U.S. Pat. No. 5,288,918. Condensation of the volatilized materials, and separation and further recovery thereof, e.g., by further distillation, can be carried out in any conventional manner, the crude aldehyde product can be passed on for further purification and separation, if desired, and any recovered reactants, e.g., olefinic starting material and syngas, can be recycled in any desired manner to the hydroformylation zone (reactor). The recovered metal catalyst containing raffinate of such membrane separation or recovered non-volatilized metal catalyst containing residue of such vaporization separation can be recycled, to the hydroformylation zone (reactor) in any conventional manner desired. Gas recycle processes, which are known to those skilled in the art, can also be employed if desired.

In a preferred embodiment, the hydroformylation reaction fluid includes any fluid derived from any corresponding hydroformylation process that contains at least some amount of four different main ingredients or components, i.e., the aldehyde product, a metal-bidentate ligand complex catalyst, free bidentate ligand and a solvent for the catalyst and the free ligand. The hydroformylation reaction mixture compositions can and normally will contain additional ingredients such as those that have either been deliberately employed in the hydroformylation process or formed in situ during said process. Examples of such additional ingredients include unreacted olefin starting material, carbon monoxide and hydrogen gases, and in situ formed by-products, such as saturated hydrocarbons and/or unreacted isomerized olefins corresponding to the olefin starting materials, ligand degradation compounds, and high boiling liquid aldehyde condensation by-products, as well as other inert co-solvent type materials or hydrocarbon additives, if employed.

The reaction conditions of the hydroformylation processes may include any suitable type hydroformylation conditions previously employed for producing aldehydes. The total gas pressure of hydrogen, carbon monoxide and olefin starting compound of the hydroformylation process may range from 1 to 69,000 kilopascals (kPa). In general, however, it is preferred that the process be operated at a total gas pressure of hydrogen, carbon monoxide and olefin starting compound of less than 14,000 kPa and more preferably less than 3,400 kPa. The minimum total pressure is limited predominately by the amount of reactants necessary to obtain a desired rate of reaction. More specifically, the carbon monoxide partial pressure of the hydroformylation process is preferably from 1 to 6,900 kPa, and more preferably from 21 to 5,500 kPa, while the hydrogen partial pressure is preferably from 34 to 3,400 kPa and more preferably from 69 to 2,100 kPa. In general, the molar ratio of gaseous $H_2$:CO may range from 1:10 to 100:1 or higher, the more preferred molar ratio being from 1:10 to 10:1.

In general, the hydroformylation process may be conducted at any operable reaction temperature. Advantageously, the hydroformylation process is conducted at a reaction temperature from −25° C. to 200° C., preferably from ambient, e.g., 23° C., to 120° C.

The hydroformylation processes may be carried out using one or more suitable reactors such as, for example, a fixed bed reactor, a fluid bed reactor, a continuous stirred tank reactor (CSTR) or a slurry reactor. The reaction zone employed may be a single vessel or may comprise two or more discrete vessels. The separation zone employed may be a single vessel or may comprise two or more discrete vessels. The reaction zone(s) and separation zone(s) employed herein may exist in the same vessel or in different vessels. For example, reactive separation techniques, such as reactive distillation and reactive membrane separation, may occur in the reaction zone(s).

The hydroformylation process can be conducted with recycle of unconsumed starting materials if desired. The reaction can be conducted in a single reaction zone or in a plurality of reaction zones, and in series or in parallel. The reaction steps may be effected by the incremental addition of one of the starting materials to the other. Also, the reaction steps can be combined by the joint addition of the starting materials. When complete conversion is not desired or not obtainable, the starting materials can be separated from the product, for example by distillation, and the starting materials then recycled back into the reaction zone.

The hydroformylation processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The hydroformylation processes of this invention may be conducted in one or more steps or stages. The exact number of reaction steps or stages will be governed by the best compromise between capital costs and achieving high catalyst selectivity, activity, lifetime and ease of operability, as well as the intrinsic reactivity of the starting materials in question and the stability of the starting materials and the desired reaction product to the reaction conditions.

In one embodiment, the hydroformylation process useful in this invention may be carried out in a multi-staged reactor such as described, for example, in U.S. Pat. No. 5,728,893. Such multi-staged reactors can be designed with internal, physical barriers that create more than one theoretical reactive stage per vessel.

It is generally preferred to carry out the hydroformylation processes in a continuous manner. Continuous hydroformylation processes are well known in the art. The continuous process can be carried out in a single pass mode, i.e., wherein a vaporous mixture comprising unreacted olefinic starting material(s) and vaporized aldehyde product is removed from the liquid reaction mixture from which the aldehyde product is recovered and make-up olefinic starting material(s), carbon monoxide and hydrogen are supplied to the liquid reaction medium for the next single pass through without recycling the unreacted olefinic starting material(s). Such types of recycle procedure are well known in the art and may involve the liquid recycling of the metal-organophosphorous complex catalyst fluid separated from the desired aldehyde reaction product(s), such as disclosed, for example, in U.S. Pat. No. 4,148,830 or a gas recycle procedure such as disclosed, for example, in U.S. Pat. No. 4,247,486, as well as a combination of both a liquid and gas recycle procedure if desired. The most preferred hydroformylation process comprises a continuous liquid catalyst recycle process. Suitable liquid catalyst recycle procedures are disclosed, for example, in U.S. Pat. Nos. 4,668,651; 4,774,361; 5,102,505 and 5,110,990.

In one embodiment, the aldehyde product mixtures may be separated from the other components of the crude reaction mixtures in which the aldehyde is produced by any suitable method such as, for example, solvent extraction, crystallization, distillation, vaporization, wiped film evaporation, falling film evaporation, phase separation, filtration, or any combination thereof. It may be desired to remove the aldehyde product from the crude reaction mixture as it is formed through the use of trapping agents as described in WO 88/08835. One method for separating the aldehyde from the other components of the crude reaction mixtures is by membrane separation, which is described, for example in U.S. Pat. Nos. 5,430,194 and 5,681,473.

As indicated above, aldehyde product may be recovered from the reaction mixtures. For example, the recovery techniques disclosed in U.S. Pat. Nos. 4,148,830 and 4,247,486 can be used. For instance, in a continuous liquid catalyst recycle process the portion of the liquid reaction mixture (containing aldehyde product, catalyst, etc.), i.e., reaction fluid, removed from the reaction zone can be passed to a separation zone, e.g., vaporizer/separator, wherein the desired aldehyde product can be separated via distillation, in one or more stages, under normal, reduced or elevated pressure, from the liquid reaction fluid, condensed and collected in a product receiver, and further purified if desired. The remaining non-volatilized catalyst containing liquid reaction mixture may then be recycled back to the reactor as may if desired any other contained materials, e.g., unreacted olefin, together with any hydrogen and carbon monoxide dissolved in the liquid reaction after separation thereof from the condensed aldehyde product, e.g., by distillation in any conventional manner. If desired, the aldehyde product may be separated from the catalyst-containing reaction mixture under reduced pressure and at low temperatures so as to lessen degradation of the organophosphorous ligand and reaction products.

More particularly, distillation and separation of the desired aldehyde product from the metal-bidentate complex catalyst containing reaction fluid may take place at any suitable temperature desired. In general, it is preferred that such distillation take place at relatively low temperatures, such as below 150° C., and more preferably at a temperature in the range of from 50° C. to 140° C.

Product

The aldehyde product of the ethylene hydroformylation is propionaldehyde.

Specific Embodiments

Equipment and Procedure

The following examples are for illustrative purposes only. All parts and percentages are by weight unless otherwise indicated. Synthetic procedures are performed using dry solvents in a nitrogen-purged glove box or under nitrogen or argon using Schlenk techniques. Commercially available reagents are purchased from Aldrich, Strem, or Acros and used as received. Multinuclear NMR spectra ($^{1}H$, $^{13}C$, $^{31}P$) were collected on a Varian MR-400 or a Bruker 400 MHz spectrometer. Proton and $^{13}C$ NMR chemical shifts are referenced in parts per million relative to residual solvent peaks; phosphorus-31 chemical shifts were referenced externally to 85% $H_3PO_4$ (0 ppm).

Preparation of 2,2'-bis[(bis(diethyl 3,4-pyrroledicarboxylate)phosphino)-oxy]-5,5',6,6',7,7',8,8'-octahydro-1,1'-binaphthalene

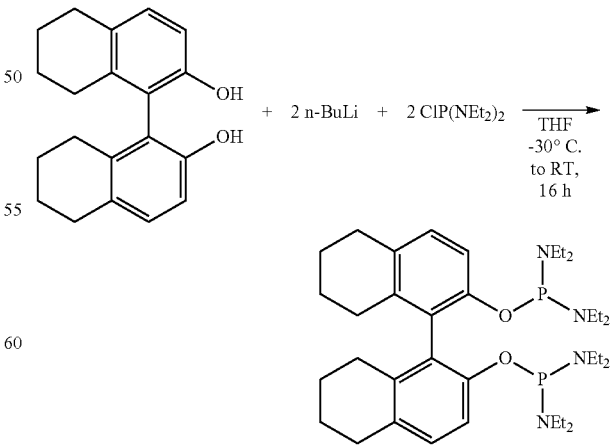

5,5',6,6',7,7',8,8'-Octahydro-1,1'-bi-2-naphthol (1.105 g, 3.754 mmol) was dissolved in 60 mL of dry THF and chilled at −30° C. for 1 hour. The solution was removed from the freezer and a 1.6 M solution of n-butyllithium in hexanes (5.0 mL, 8.0 mmol, 2.1 equivalents) was slowly added with stirring. The solution was allowed to warm slowly, whereupon a white precipitate began to form. After two hours of stirring, the reaction mixture was returned to the freezer for 30 minutes to chill. A separate solution of bis(diethylamino)chlorophosphine (1.7 mL, 8.1 mmol, 2.2 equivalents) in 10 mL of THF was prepared and also placed in the freezer at −30° C. for 30 minutes. The cold phosphine solution was added dropwise with stirring to the cold lithium salt solution. The reaction mixture was allowed to warm slowly, and was stirred at room temperature overnight. The reaction mixture was pumped down to dryness and then triturated with 30 mL of hexanes. The resultant yellow oil was dissolved in 60 mL of toluene and filtered through Celite. The filtrate was used in the next step of the reaction without further purification or characterization.

Preparation of 2,2'-bis((dichlorophosphino)oxy)-5,5',6,6',7,7',8,8'-octahydro-1,1'-binaphthalene

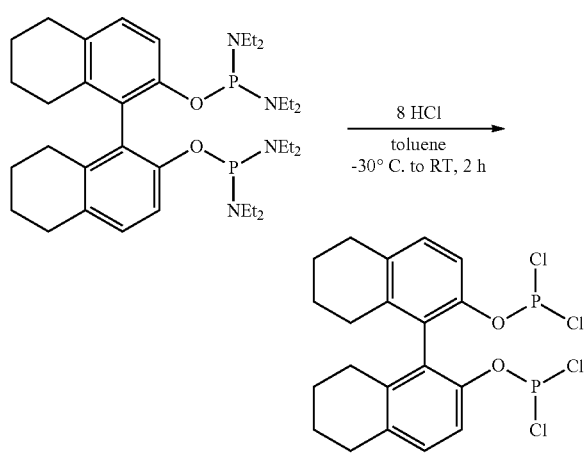

The toluene solution from the previous step was chilled in the glove box freezer at −30° C. for 1 hour. A 2.0 M solution of HCl in diethyl ether (15.0 mL, 30.0 mmol, 8 equivalents) was added with stirring to the cold solution over a period of about five minutes. A copious amount of white solids formed during the addition. The reaction mixture was allowed to warm to room temperature and stirred for an additional 2 hours. The mixture was filtered through Celite and pumped down to dryness. The resultant yellow oil was used in the next step of the reaction without further purification.

Preparation of Ligand 1

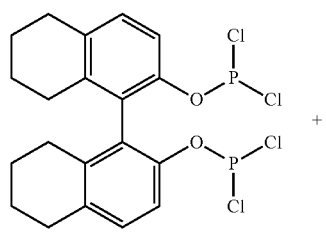

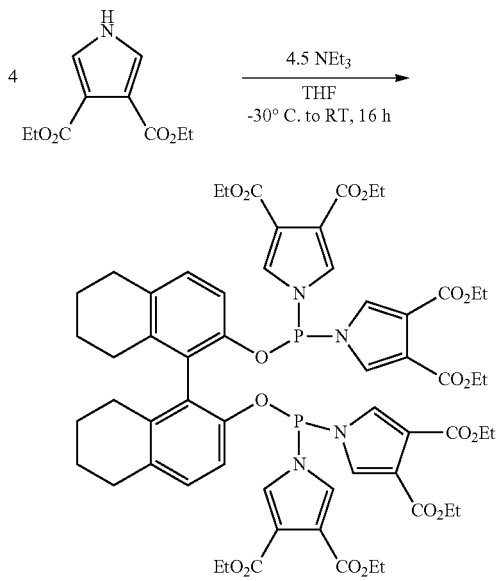

The 2,2'-bis((dichlorophosphino)oxy)-5,5',6,6',7,7',8,8'-octahydro-1,1'-binaphthalene from the previous step was dissolved in 80 mL of dry THF. Diethyl 3,4-pyrroledicarboxylate (3.17 g, 15.0 mmol, 4 equivalents) was added to the solution with stirring. No apparent reaction occurred. The solution was placed in the glove box freezer at −30° C. for 1 hour to chill. Triethylamine (2.4 mL, 17 mmol, 4.5 equivalents) was added dropwise with stirring to the cold solution over a period of five minutes. A copious amount of white precipitate formed in the reaction mixture. The reaction mixture was allowed to warm to room temperature. After stirring overnight, the mixture was filtered through Celite, and the filter cake washed with THF. The filtrate was pumped down to dryness to yield a yellow oil. The crude material was heated in 60 mL of toluene at 60° C. until all of the material dissolved. The warm solution was placed in the glove box freezer at −30° C. overnight, during which time crystals of diethyl 3,4-pyrroledicarboxylate deposited from solution. These were removed by filtration, and the filtrate pumped down to dryness. The solid residue was heated in 60 mL of hexanes at 60° C. for 2 hours, after which Ligand 1 was collected as a fine white powder. Total mass collected: 1.138 g (0.9521 mmol, 25% yield). $^1$H NMR (400 MHz, $C_6D_6$) δ 7.31 (s, 4H, CH-pyrrole), 7.16 (s (under $C_6HD_5$ peak), 4H, CH-pyrrole), 6.90 (d, $J_{HH}$=8.4 Hz, Ar—H), 6.64 (d, $J_{HH}$=8.0 Hz, Ar—H), 4.13-4.21 (m, 16H, O—$CH_2$), 2.50-2.83 (m, 4H, $CH_2$), 2.00-2.24 (m, 4H, $CH_2$), 1.36-1.65 (m, 8H, $CH_2$), 1.10 (t, 12H, $CH_3$), 1.07 (t, 12H, $CH_3$); $^{13}C\{^1H\}$ NMR (100.6 MHz, $CDCl_3$) δ 162.9 (d, $J_{PC}$=3.6 Hz, C=O), 147.7 (t, $J_{PC}$=6.3 Hz, C—O—P), 138.2 (s, Ar), 136.3 (s, Ar), 131.2 (s, Ar), 126.7 (quartet, $J_{PC}$=8.0 Hz, CH-pyrrole), 125.7 (s, Ar), 120.5 (d, $J_{PC}$=15.0 Hz, Ar), 116.6 (t, $J_{PC}$=4.6 Hz, C-pyrrole), 60.9 (s, O—$CH_2$), 29.3 (s, $CH_2$), 27.9 (s, $CH_2$), 22.6 (s, $CH_2$), 14.4 (s, $CH_3$); $^{31}P\{^1H\}$ NMR (162 MHz, $C_6D_6$) δ 108.7 (s) ppm.

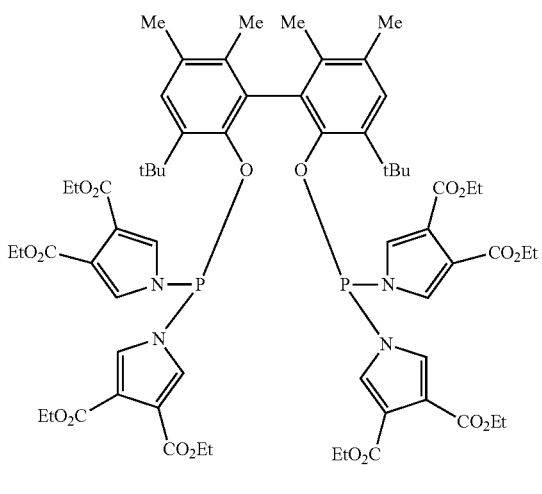 [SMILES: CCOC(=O)c1cn(P(Oc2c(C(C)(C)C)cc(C)c(C)c2-c2c(C)c(C)cc(C(C)(C)C)c2OP(n2cc(C(=O)OCC)c(C(=O)OCC)c2)n2cc(C(=O)OCC)c(C(=O)OCC)c2)n2cc(C(=O)OCC)c(C(=O)OCC)c2)cc1C(=O)OCC]

Preparation of Ligand 2

A procedure similar to that described for Ligand 1 was utilized to prepare Ligand 2. Total mass collected: 0.250 g (0.199 mmol, 7% yield). $^1$H NMR (400 MHz, CDCl$_3$) 7.34 (s, 4H, CH-pyrrole), 7.12 (s, 4H, CH-pyrrole), 7.08 (s, 2H, Ar—H), 4.23-4.32 (m, 16H, O—CH$_2$), 1.98 (s, 6H, Ar—CH$_3$), 1.58 (s, 6H, Ar—CH$_3$), 1.29-1.35 (m, 24H, CH$_2$CH$_3$), 1.15 (s, 18H, C(CH$_3$)$_3$); $^{13}$C{$^1$H} NMR (100.6 MHz, CDCl$_3$) δ 162.9 (d, J$_{PC}$=4.6 Hz, C=O), 150.0 (t, J$_{PC}$=4.3 Hz, C—O—P), 137.7 (s, Ar), 136.6 (s, Ar), 134.4 (s, Ar), 131.1 (s, Ar), 127.3 (t, J$_{PC}$ 9.9 Hz, CH-pyrrole), 126.9 (t, J$_{PC}$=9.1 Hz, CH-pyrrole), 120.3 (s, Ar), 119.3 (s, C-pyrrole), 60.8 (d, J$_{PC}$=5.5 Hz, O—CH$_2$), 34.3 (s, Ar—CH$_3$), 30.2 (s, C(CH$_3$)$_3$), 20.2 (s, Ar—CH$_3$), 17.3 (t, J$_{PC}$=2.6 Hz, C(CH$_3$)$_3$), 14.4 (d, J$_{PC}$=5.6 Hz, CH$_2$CH$_3$); $^{31}$P{$^1$H} NMR (162 MHz, CDCl$_3$) δ 100.3 (s) ppm.

Preparation of 5,5',6,6'-tetramethyl-2,2'-biphenol

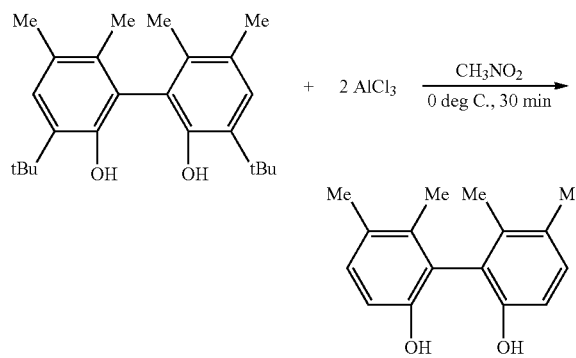

The biphenol was prepared according to the procedure (Hua, Z., Vassar, V. C., Ojima, I., "Synthesis of New Chiral Monodentate Phosphite Ligand and Their Use in Catalytic Asymmetric Hydrogenation", Organic Letters, 5 (2003), 3831-3834) with slight modifications from commercially available 3,3'-di-t-butyl-5,5',6,6'-tetramethyl-1,1'-biphenyl-2,2'-diol (rac-BIPHEN. Yield: 3.428 g (14.1 mmol, 56.1%). $^1$H NMR (400 MHz, CDCl$_3$): δ 7.12 (d, J$_{HH}$=8 Hz, 2H, Ar—H), 6.81 (d, J$_{HH}$=8 Hz, 2H, Ar—H), 4.51 (s, 2H, OH), 2.25 (s, 6H, CH$_3$), 1.89 (s, 6H, CH$_3$) ppm.

Preparation of Ligand 3

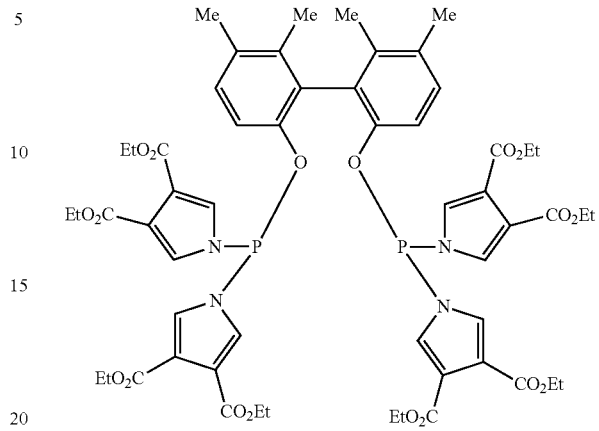

The 5,5',6,6'-tetramethyl-2,2'-biphenol prepared above was utilized in a procedure similar to that described for Ligand 1 to produce Ligand 3. Yield: 2.46 g (2.16 mmol, 50.9%). $^1$H NMR (400 MHz, C$_6$D$_6$) δ 7.21 (dm, J$_{PH}$=22 Hz, J$_{NH}$=1 Hz, 8H, N—CH), 6.93 (d, J$_{HH}$=8 Hz, 2H, Ar—H), 6.67 (d, J$_{HH}$=8 Hz, 2H, Ar—H), 4.22-4.09 (m, 16H, CH$_2$CH$_3$), 2.09 (s, 6H, Ar—CH$_3$), 1.70 (s, 6H, Ar—CH$_3$), 1.10 (t, J$_{HH}$=7 Hz, 12H, CH$_2$CH$_3$), 1.07 (t, J$_{HH}$=7 Hz, 12H, CH$_2$CH$_3$); $^{31}$P{$^1$H} NMR (162 MHz, C$_6$D$_6$) δ 108.7 ppm.

Preparation of Chlorodipyrrolylphosphine

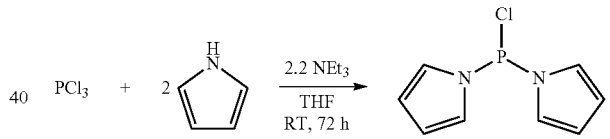

Chlorodipyrrolylphosphine was prepared in a similar manner to that described in the reference (van der Slot, S. C., Duran, J., Luten, J., Kamer, P. C. J., van Leeuwen, P. W. N. M., "Rhodium-Catalyzed Hydroformylation and Deuterioformylation with Pyrrolyl-Based Phosphorus Amidite Ligands: Influence of Electronic Ligand Properties", Organometallics, 21 (2002), 3873-3883). $^1$H NMR (400 MHz, C$_6$D$_6$) δ 6.80 (m, 4H, CHCHNP), 6.18 (m, 4H, CHCHNP); $^{31}$P{$^1$H} NMR (162 MHz, C$_6$D$_6$) δ 105.3 ppm.

Preparation of Ligand 4

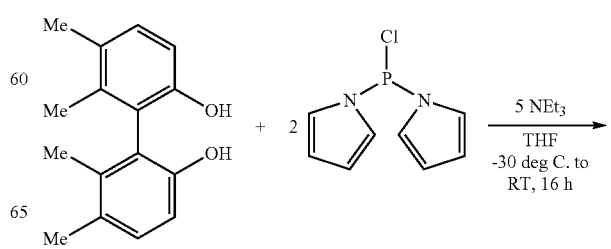

-continued

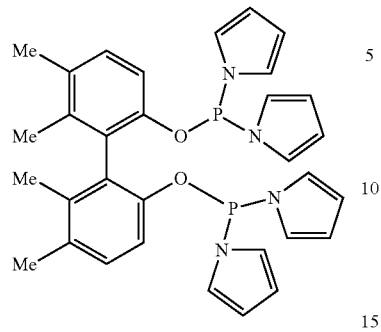

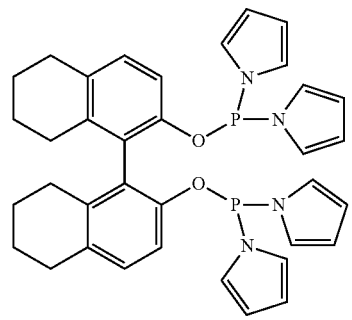

Chlorodipyrrolylphosphine (1.67 g, 8.42 mmol, 2 equivalents) and 5,5',6,6'-tetramethyl-1,1'-biphenyl-2,2'diol (1.02 g, 4.21 mmol) were dissolved in 80 mL of THF and chilled at −30° C. for 1 hour. Triethylamine (3.0 mL, 22 mmol, 5.2 equivalents) was added dropwise to the cold solution with stirring. A copious amount of white precipitate formed in solution during the addition. The reaction mixture was allowed to warm to room temperature and stir overnight. The reaction mixture was filtered through Celite and the filter cake was washed with an additional 20 mL of THF. The filtrate was pumped down to dryness and then triturated thoroughly with 160 mL of hexanes. The mixture was filtered and the filtrate pumped down to dryness to yield the desired product as a white powder. Yield: 1.69 g (2.98 mmol, 70.8%). $^1$H NMR (400 MHz, C$_6$D$_6$) δ 6.82 (d, J$_{HH}$=8 Hz, 2H, Ar—H), 6.74-6.69 (m, 10H, overlapping signals for Ar—H and CHCHNP), 6.22 (m, 8H, CHCHNP), 1.96 (s, 6H, CH$_3$), 1.78 (s, 6H, CH$_3$); $^{13}$C{$^1$H} (101 MHz, C$_6$D$_6$) 150.0 (d, $^2$J$_{PC}$=12 Hz, C—O—P), 138.1 (s, Ar—C), 133.8 (s, Ar—C), 130.7 (s, Ar—CH), 129.7 (t, $^3$J$_{PC}$=2 Hz, Ar—C), 121.1 (dd, $^3$J$_{PC}$=16 Hz, J=3 Hz, CHCHNP), 116.4 (d, $^3$J$_{PC}$=12 Hz, Ar—CH) 112.3 (dt, $^2$J$_{PC}$=9 Hz, J=2 Hz, CHCHNP), 19.5 (s, CH$_3$), 16.4 (s, CH$_3$); $^{31}$P{$^1$H} NMR (162 MHz, C$_6$D$_6$) δ 109.5 ppm Preparation of Ligand 5

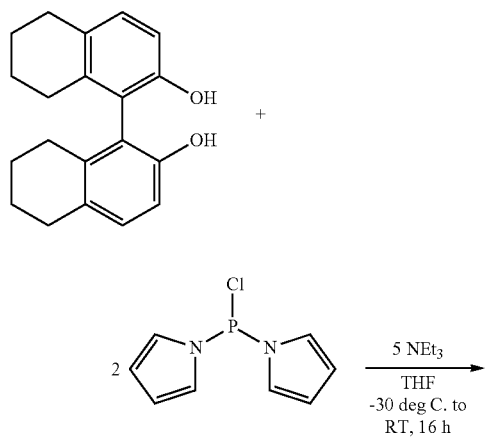

A procedure similar to that described for Ligand 4 was used to prepare Ligand 5. Yield: 1.94 g (3.13 mmol, 81.5%). $^1$H NMR (400 MHz, C$_6$D$_6$) δ 6.80-6.75 (m, 8H, overlapping signals for Ar—H and CHCHNP), 6.68 (m, 4H, CHCHNP), 6.25-6.21 (m, 8H, CHCHNP), 2.52 (m, 6H, CH$_2$), 2.47-2.39 (m, 2H, CH$_2$), 2.20-2.13 (m, 2H, CH$_2$), 1.51-1.38 (m, 8H, CH$_2$); $^{13}$C{$^1$H} (101 MHz, C$_6$D$_6$) 149.4 (d, $^2$J$_{PC}$=12 Hz, C—O—P), 138.3 (s, Ar—C), 134.6 (s, Ar—C), 130.5 (s, Ar—CH), 128.7 (t, $^3$J$_{PC}$=2 Hz, Ar—C), 121.9 (dd, $^3$J$_{PC}$=16 Hz, J=6 Hz, CHCHNP), 117.4 (d, $^3$J$_{PC}$=11 Hz, Ar—CH) 113.0 (dt, $^2$J$_{PC}$=18 Hz, J=2 Hz, CHCHNP), 30.5 (s, CH$_2$), 28.3 (s, CH$_2$), 23.5 (s, CH$_2$), 23.4 (s, CH$_2$); $^{31}$P{$^1$H} NMR (162 MHz, C$_6$D$_6$) δ 109.2 ppm.

Preparation of bis(indolyl)chlorophosphine

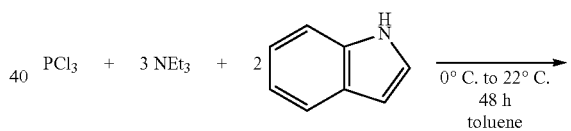

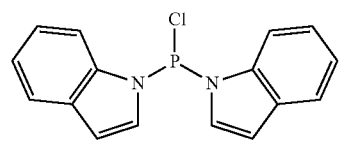

Triethylamine (5.0 mL, 36 mmol) and PCl$_3$ (1.0 mL, 11.5 mmol) were combined in 100-mL of toluene to form a pale yellow solution. The solution was transferred to a 250-mL Schlenk flask in an ice/water bath. A solution of indole (2.69 g, 23.0 mmol) in 25 mL of toluene was added via syringe pump to the cooled triethylamine/PCl$_3$ solution at a dispense rate of 0.5 mL/min. A copious amount of white solid formed in the yellow solution during the addition. Following the addition, the reaction mixture was allowed to stir at room temperature over the weekend. The reaction mixture was concentrated to half its volume under vacuum and filtered through Celite under nitrogen. The filtrate was pumped down to dryness, and the resultant yellow oil was triturated with 30 mL of hexanes and dried under vacuum for one hour. Yield: 2.77 g (9.27 mmol, 81%). Purity was approximately 94% by phosphorus NMR, δ$^{31}$P=104 ppm.

Preparation of Ligand 6

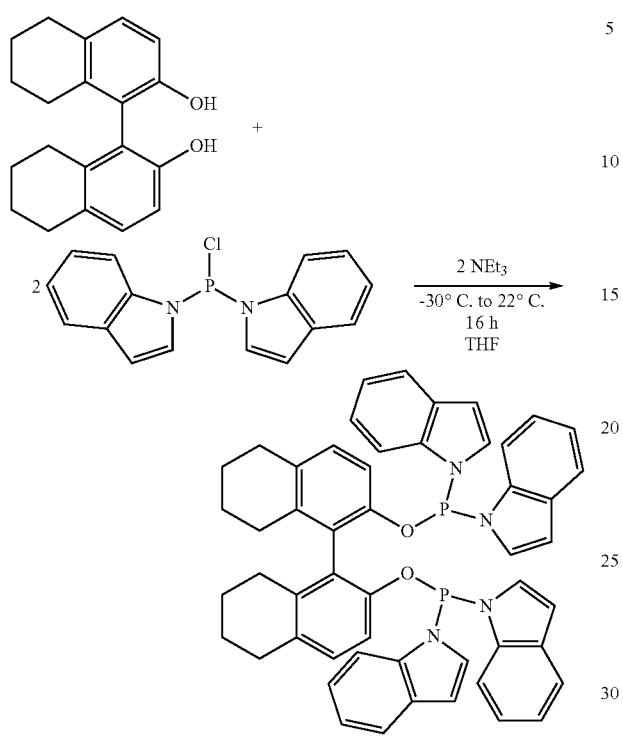

Bis(indolyl)chlorophosphine (2.77 g, 9.27 mmol) was combined with 5,5',6,6',7,7',8,8'-octahydro-1,1'-bi-2-naphthol (1.36 g, 4.62 mmol), and 80 mL of dry THF to form a colorless solution which was chilled in a freezer (−30° C.). Triethylamine (2.0 mL, 14.3 mmol) was added dropwise with stirring to the cold solution, whereupon copious amount of white precipitate formed immediately. After stirring overnight at room temperature, the reaction mixture was filtered through Celite and the filtrate pumped down to dryness. The resultant yellow oil was triturated with 40 mL of hexanes, dissolved in toluene (60 mL) and filtered through Celite. The filtrate was concentrated to a volume of 20 mL under vacuum and placed in a freezer (−30° C.) overnight. A small amount of white solid precipitated and was removed via filtration. The filtrate was pumped down to dryness and the resultant oily solid was slurried in 60 mL of hexanes, resulting in precipitation of a white solid. The mixture was filtered, and the filtrate was pumped down to dryness to yield a white powder. The white oily solids left behind in the fit were slurried in another 60 mL of hexanes and stirred for one hour. The slurry was filtered and the filtrate was again pumped down to dryness to yield a second crop of white powder. The two crops of white powder were combined, slurried in 10 mL of hexanes, filtered, and dried in vacuo. Yield: 1.14 g, 1.39 mmol, 30%; 93% pure by $^{31}$P NMR. $^1$H NMR (400 MHz, C$_6$D$_6$) δ 7.54 (t, J$_{HH}$=8 Hz, 4H, indole-H), 7.47 (d, J$_{HH}$=8 Hz, 4H, indole-H), 7.08-7.03 (m, 8H, indole-H), 6.98-6.94 (m, 4H, indole-H), 6.73 (d, J$_{HH}$=8 Hz, 2H, naphthol-H), 6.57 (d, J$_{HH}$=8 Hz, 2H, naphthol-H) 6.38-6.37 (m, 4H, indole-H), 2.44-2.33 (m, 6H, CH$_2$), 2.16-2.09 (m, 2H, CH$_2$), 1.42-1.27 (m, 8H, CH$_2$); $^{31}$P{$^1$H} NMR (162 MHz, C$_6$D$_6$) δ 107 ppm (small impurity at 130 ppm).

Preparation of bis(3-carbomethoxyindolyl)chlorophosphine

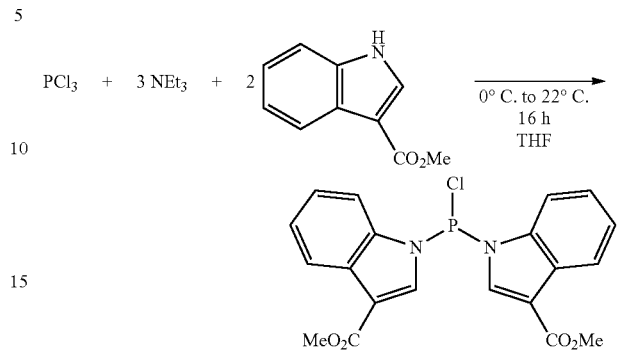

A procedure similar to that described for bis(indolyl) chlorophosphine was used to prepare bis(3-carbomethoxy-indolyl)chlorophosphine. Yield: 4.07 g (9.81 mmol, 85%). Purity was approximately 98% by phosphorus NMR, δ$^{31}$P=106 ppm.

Preparation of Ligand 7

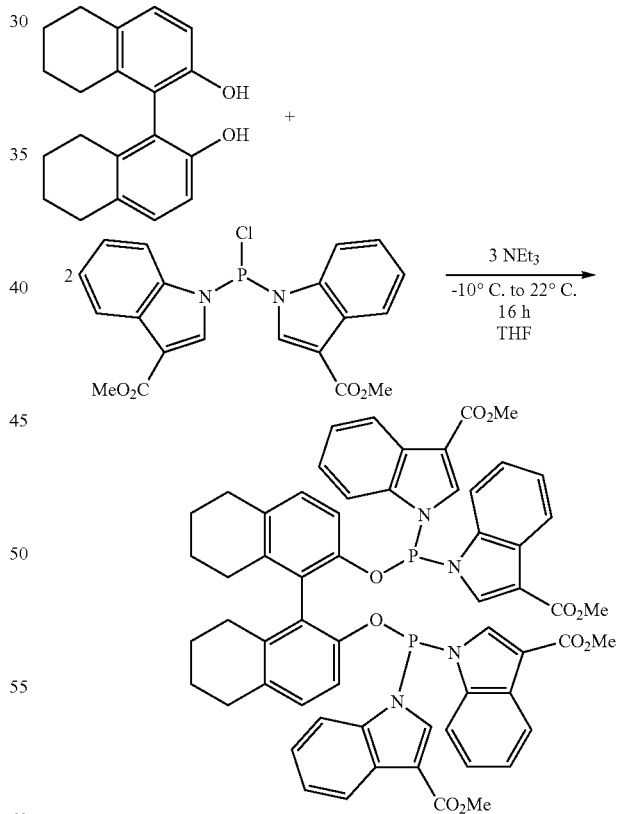

A procedure similar to that described for Ligand 6 was used to prepare Ligand 7. Yield: 0.513 g, 0.488 mmol, 9.92%. $^1$H NMR (400 MHz, CDCl$_3$) δ 8.10 (t, J$_{HH}$=8 Hz, 4H, indole-H), 7.78 (d, J$_{PH}$=24 Hz, 4H, indole-H), 7.32-7.20 (m, 8H, indole-H), 7.07 (dt, J$_{PH}$=24 Hz, J$_{HH}$=8 Hz, 4H, indole-H), 6.80 (d, J$_{HH}$=8 Hz, 2H, naphthol-H), 6.61 (d, $J_{HH}$=8 Hz, 2H, naphthol-H), 3.85 (d, $J_{HH}$=6 Hz, 12H, CH$_3$), 2.66-2.47 (m, 4H, CH$_2$), 2.26-2.06 (m, 4H, CH$_2$), 1.63-1.44 (m, 8H, CH$_2$); $^{31}$P{$^1$H} NMR (162 MHz, CDCl$_3$) δ 106 ppm (100%).

Preparation of Ligand 8

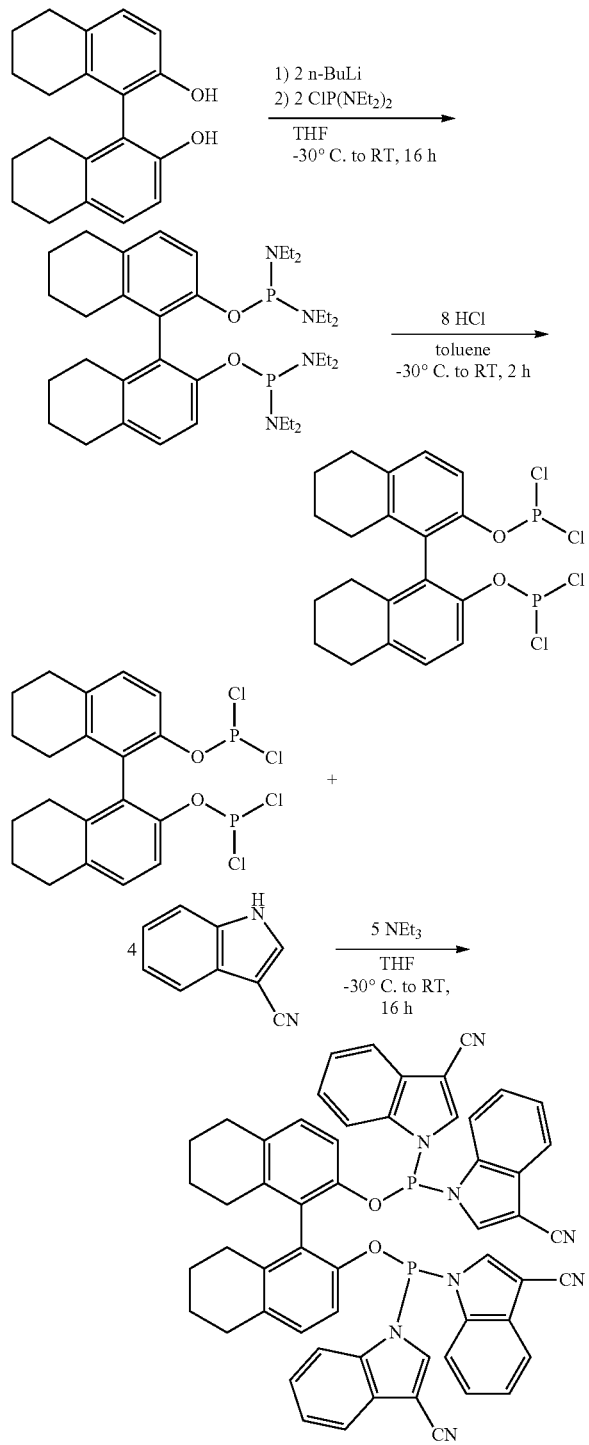

A solution of 5,5',6,6',7,7',8,8'-octahydro-1,1'-bi-2-naphthol (0.845 g, 2.87 mmol) in 70 mL of THF was chilled in a freezer. A 1.6 M solution of n-butyllithium in hexanes (3.8 mL, 6.1 mmol) was slowly added with stirring. The reaction mixture was stirred at room temperature for 2 hours, and then returned to the freezer for 30 minutes to chill. Bis(diethylamino)chlorophosphine (1.3 mL, 6.2 mmol) was added dropwise with stirring to the cold mixture. After stirring at room temperature overnight, the reaction mixture was pumped down to dryness and then triturated with 30 mL of hexanes. The resultant yellow oil was dissolved in 80 mL of toluene and filtered through Celite. The filtrate was chilled in a freezer at −30° C. for one hour. A 2.0 M solution of HCl in diethyl ether (11.5 mL, 23.0 mmol) was added to the cold solution with stirring over a period of 5 minutes. A copious amount of white solid formed during the addition. The reaction mixture was allowed to warm to room temperature and was stirred for a further 2 hours. The reaction mixture was filtered through Celite and the toluene filtrate was pumped down to dryness. The resultant yellow oil was triturated with 30 mL of hexanes and further dried under vacuum for one hour The oil was dissolved in 50 mL of THF and stirred at room temperature. A solution of 3-Cyanoindole (1.49 g, 16.9 mmol) in 30 mL THF was added slowly. The mixture was placed in the freezer at −30° C. to chill. Triethylamine (2.0 mL, 14 mmol) was added dropwise with stirring to the cold solution over a period of five minutes. A copious amount of white precipitate formed in the reaction mixture. The reaction mixture was allowed to warm to room temperature and was stirred overnight. The reaction mixture was then filtered through Celite and the filtrate was pumped down to dryness. The resultant yellow oil was triturated with 40 mL of hexanes and then taken up in 60 mL of toluene and filtered. The filtrate was pumped down to dryness to yield a white powder. A $^1$H NMR spectrum of the material showed a large amount of toluene present in the material, which did not disappear upon repeated triturations with hexanes and drying of the sample under vacuum for several hours. The white powder was slurried in Et$_2$O (10 mL), collected by filtration and washed with 5 mL of hexanes. The Et$_2$O and hexanes washings were repeated twice more, greatly decreasing the yield, yet improving the purity. The sample was dried overnight under vacuum, yet some toluene (approx. 0.3 equivalents) and ether (approx. 0.1 equivalents) remained in the sample. Yield: 0.312 g (0.340 mmol, 13%). $^1$H NMR (400 MHz, C$_6$D$_6$) δ 7.65 (d, $J_{HH}$=8 Hz, 1H, indole-CH), 7.46-7.42 (m, 2H, indole-H), 7.39 (d, $J_{HH}$=8 Hz, 2H, indole-H), 7.15-7.13 (m, 4H, indole-H), 7.06 (d, $J_{HH}$=8 Hz, 2H, naphthol-H), 6.99-6.98 (m, 2H, indole-H), 6.89-6.76 (m, 8H, indole-H), 6.55 (d, $J_{HH}$=8 Hz, 2H, naphthol-H), 2.71-2.64 (m, 2H, CH$_2$), 2.51-2.44 (m, 2H, CH$_2$), 2.15-1.96 (m, 4H, CH$_2$), 1.47-1.24 (m, 8H, CH$_2$); $^{31}$P{$^1$H} NMR (162 MHz, C$_6$D$_6$) δ 106 (s, 94%) ppm (impurity at 107 ppm).

Preparation of bis(3-methylindolyl)chlorophosphine

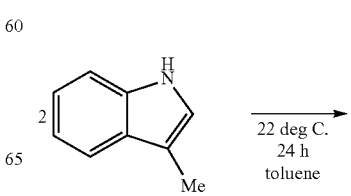

-continued

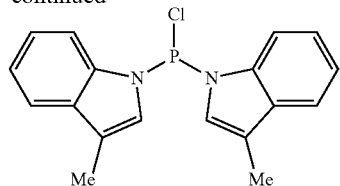

A procedure similar to that described for bis(indolyl) chlorophosphine was used to prepare bis(3-methylindolyl) chlorophosphine. Yield: 3.20 g (9.79 mmol, 85%). The material was used in the next reaction without any further purification. Purity was approximately 93% by phosphorus NMR, $\delta^{31}P=102$ ppm.

Preparation of Ligand 9

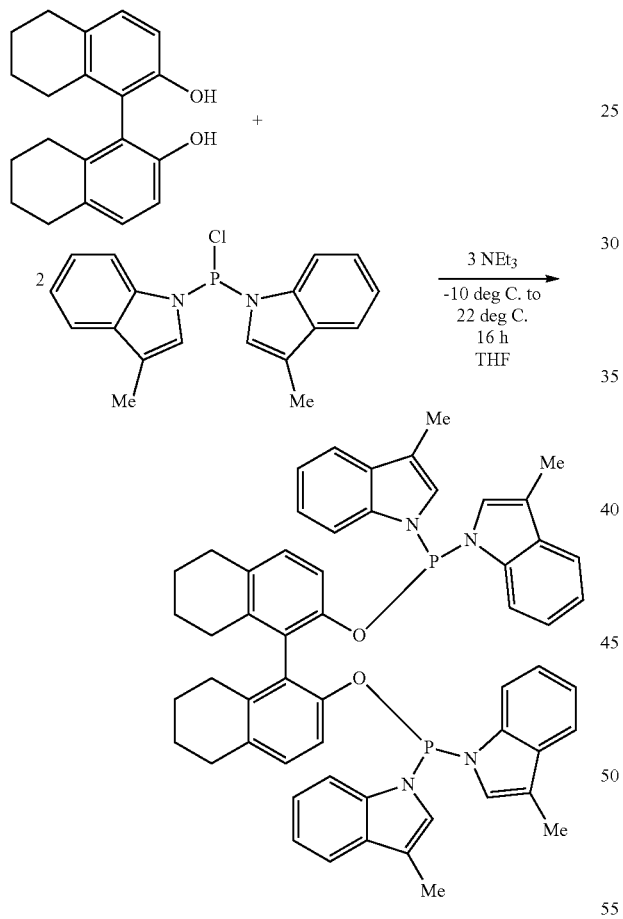

A procedure similar to that described for Ligand 6 was used to prepare Ligand 9. Yield: 3.08 g, 3.52 mmol, 71.2%. $^1$H NMR (400 MHz, C$_6$D$_6$) δ 7.59 (dd, J$_{PH}$=24 Hz, J$_{HH}$=8 Hz, 4H, indole-H), 7.41 (dd, J$_{HH}$=8 Hz, J=3 Hz, 4H, indole-H), 7.10 (td, J$_{HH}$=8 Hz, J=1 Hz, 4H, indole-H), 7.04-6.98 (m, 4H, indole-H), 6.87-6.85 (m, 4H, indole-H), 6.80 (d, J$_{HH}$=8 Hz, 2H, naphthol-H), 6.62 (d, J$_{HH}$=8 Hz, 2H, naphthol-H), 2.50-2.38 (m, 6H, CH$_2$), 2.21-2.14 (m, 2H, CH$_2$), 2.00 (dd, J=4 Hz, J=3 Hz, 12H, CH$_3$), 1.41-1.33 (m, 8H, CH$_2$); $^{31}$P{$^1$H} NMR (162 MHz, C$_6$D$_6$) δ 104 (s, 94%) ppm (impurity at 130 ppm).

Preparation of Ligand 10

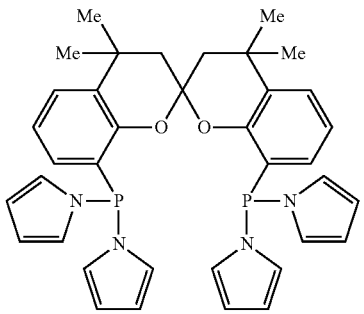 [SMILES: CC1(C)CC2(CC(C)(C)c3cccc(P(n4cccc4)n4cccc4)c3O2)Oc2c(P(n3cccc3)n3cccc3)cccc21]

8,8'-dibromo-4,4,4,4,6,6'-hexamethylspiro-2,2'-bichroman (0.65 g, 1.32 mmol) was prepared according to the procedure described in Z. Freixa, M. S. Beentjes, G. D. Batema, C. B. Dieleman, G. P. F. v. Strijdonck, J. N. H. Reek, P. C. J. Kamer, J. Fraanje, K. Goubitz and P. W. N. M. Van Leeuwen., Angew. Chem. 2003, 42, 11, 1322 and azeotropically dried with toluene and dissolved THF. The colorless solution was treated with n-butyllithium (3.3 mmol) at −78° C. for 2 hours and then chlorodipyrrolylphosphine (0.44 mL, 3.3 mmol) was added while the low temperature was maintained. The resulting mixture was allowed to warm up slowly overnight. The pale yellow solution was then filtered through neutral alumina and the filtrate volatiles removed in vacuo to afford a clear, colorless oil which eventually became a white sticky foam. The foam was dissolved in boiling methanol and left in the freezer at −30° C. for 2 hours to give Ligand 10 (0.65 g, 75%) as a white crystalline solid. $^1$H-NMR (CDCl$_3$, 25° C., 400 MHz): δ=7.18 (bs, 2H), 6.64-6.60 (m, 4H), 6.51-6.47 (m, 4H), 6.26-6.23 (m, 4H), 6.14-6.10 (m, 4H), 6.06 (m, 2H), 2.23 (s, 6H), 1.99 (d, J$_{HH}$=14.6 Hz, 2H), 1.94 (d, J$_{HH}$=14.6 Hz, 2H), 1.46 (s, 6H), 1.29 (s, 6H, H); $^{31}$P{$^1$H}-NMR (CDCl$_3$, 25° C., 160 MHz): δ=71.2; ESI-MS: [M][Na$^+$] for C$_{39}$H$_{42}$N$_4$O$_2$P$_2$ calculated 683.27, found 683.3 m/z.

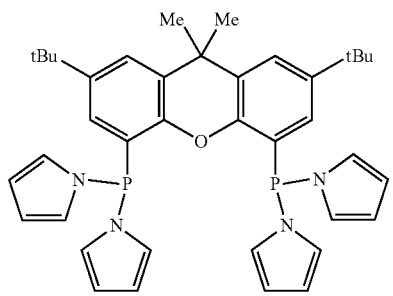 [SMILES: CC(C)(C)c1cc(P(n2cccc2)n2cccc2)c2c(c1)C(C)(C)c1cc(C(C)(C)C)cc(P(n3cccc3)n3cccc3)c1O2]

Preparation of Ligand 11

Ligand 11 was prepared according to the procedure described in Ahlers, W.; Paciello, R.; Vogt, D.; Hofmann, P. WO02083695 (A1), US2004110960 (A1), 2002.

For each reaction, the rhodium catalyst precursor (dicarbonylacetylacetonato rhodium (I)) and the appropriate ligand is weighed into a septum-capped vessel in a dry box. The solids are dissolved in dry, degassed toluene and transferred under nitrogen into a 100 ml Parr mini-reactor (30 ml runs) or an AMTEC SPR16 15 ml stainless steel reactor (5 ml runs). For the 30 ml runs, catalyst preformation is performed by heating to reaction temperature with agitation (1100 rpm) under about 240 kPa of 1:1 carbon monoxide (CO): hydrogen (syn gas) for 20-30 minutes. For the 5 ml runs, catalyst preformation is performed by heating to 80° C. under 2100.8 kPa 1:1 syn gas for 90 minutes. In each case, the reactor is vented after preformation and pressurized to final reaction pressure using a cylinder of pre-mixed ethylene, carbon monoxide and hydrogen in a 1:1:1 ratio. Each run is performed at least two times; the reported results are the averages. Pressures are given as kPa, unless otherwise indicated.

Triphenylphosphine (TPP) and tris(2,4-di-t-butylphenyl)phosphite are used as Comparative Ligand 1 and 2 respectively. All reactions are conducted in toluene with a molar ratio of 1:1:1 for the CO:H$_2$:ethylene reactants. Turnover frequency is based on gas uptake during the first 30 minutes, and is calculated as moles of product per mole of rhodium per hour. Additional reaction conditions are reported in Table 1

TABLE 1

Ethylene Hydroformylation Conditions and Results

| | Solution vol (ml) | [Rh] mM | L:Rh | 1:1:1 gas (kPa) | Temp (° C.) | TOF (×10$^{-3}$/hr) |
|---|---|---|---|---|---|---|
| Comparative Ligand 1 | 5 | 0.250 | 20 | 2100.8 | 80 | 2.23 |
| Comparative Ligand 2 | 5 | 0.250 | 20 | 2100.8 | 80 | 4.95 |
| Ligand | | | | | | |
| 1 | 30 | 0.220 | 2 | 1342.4 | 80 | 11.82 |
| 2 | 30 | 0.220 | 2 | 1342.4 | 80 | 69.55 |
| 3 | 30 | 0.088 | 2 | 1342.4 | 80 | 72.73 |
| 4 | 30 | 0.088 | 2 | 1342.4 | 80 | 117.05 |
| 5 | 30 | 0.088 | 2 | 1342.4 | 70 | 88.64 |
| 6 | 30 | 0.220 | 2 | 1342.4 | 80 | 27.73 |
| 7 | 30 | 0.220 | 2 | 1342.4 | 80 | 81.36 |
| 8 | 30 | 0.220 | 2 | 1342.4 | 80 | 60.45 |
| 9 | 30 | 0.220 | 2 | 1342.4 | 80 | 37.27 |
| 10 | 5 | 0.250 | 20 | 2100.8 | 80 | 17.10 |
| 11 | 5 | 0.250 | 20 | 2100.8 | 80 | 20.30 |

RESULTS AND CONCLUSIONS

The results in Table 1 clearly show that catalysts comprised of rhodium and the ligands of the present invention are much more active than rhodium-TPP under similar conditions. For example, the reaction featuring a catalyst promoted by Ligand 4 is about 50 times as active as rhodium-TPP (Comparative Ligand 1) while only utilizing ⅓ of the rhodium concentration of the comparative example. Likewise the rhodium-Ligand 5 catalyst is about 40 times as active as rhodium-TPP, while only utilizing ⅓ of the rhodium concentration and a reaction temperature that is 10° C. lower. Thus the present invention would allow industrial processes to meet production targets while operating with much less rhodium and at lower temperatures relative to a rhodium-TPP catalyst.

Moreover Table 1 shows that catalyst promoted by the ligands of the present invention are much more active for ethylene hydroformylation than rhodium promoted by the bulky triarylphosphite, tris(2,4-di-t-butylphenyl)phosphite. Catalysts promoted by bulky triarylphosphites are well known to be extremely active for the hydroformylation of many olefins (e.g. J. Organomet. Chem., 1983, 258, 343; J. Organomet. Chem., 1991, 421, 121; J. Chem Soc. Chem. Commun., 1991, 1096). This illustrates that the activity of a rhodium catalyst promoted by a particular ligand for the hydroformylation of other olefins is not predictive for the hydroformylation of ethylene.

It is specifically intended that the present invention not be limited to the embodiments and illustrations contained herein, but include modified forms of those embodiments including portions of the embodiments and combinations of elements of different embodiments as come within the scope of the following claims.

We claim:

1. A process for the hydroformylation of ethylene with a transition metal catalyst promoted with a bidentate ligand of Formula I, II and III:

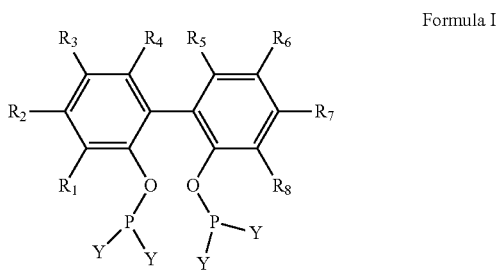

in which both $R_1$ and $R_8$ are hydrogen or a hydrocarbyl group of $C_1$ to $C_4$; $R_2$-$R_7$ and $R_9$-$R_{24}$ are independently a hydrogen, a hydrocarbyl group, an aromatic ring, a heteroaromatic ring or a halogen atom, or a heterocarbyl group selected from the groups consisting of $NR_2$, $OR$ and $SR$, where R is a hydrocarbyl group of $C_1$ to $C_{20}$, or heterohydrocarbyl group having 1 to 20 atoms, each independently selected from C or a heteroatom, wherein each heteroatom is independently O, S, Si, Ge, P, or N, and may themselves be substituted or unsubstituted as required by the valency of the heteroatom, $R_2$-$R_7$ and $R_9$-$R_{24}$ may optionally comprise cycloaliphatic or aryl groups fused to the biaryl moiety such as:

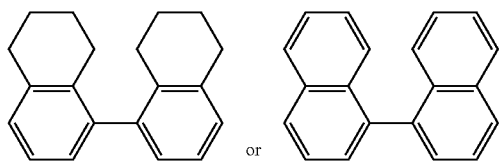

for Formula I, II, or III, each aryl, heteroaryl, hydrocarbyl, heterohydrocarbyl, hydrocarbylene, and heterohydrocarbylene group independently is unsubstituted or substituted with one or more substituents $R^v$ each independently a halogen atom, polyfluoroalkyl substitution, unsubstituted $C_1$ to $C_{18}$ alkyl, $F_3C$—, $F_2HCO$—, $F_3CO$—, $R_3Si$, $R_3Ge$, RO, RS, RS(O), RS(O)$_2$, $R_2P$, $R_2N$, $R_2C$=N, NC, RC(O)O, ROC(O), RC(O)N(R), or $R_2NC(O)$, or two of the $R^v$ are taken together to form an un unsubstituted $C_1$ to $C_{18}$ alkylene, wherein each R independently is an unsubstituted $C_1$ to $C_{18}$ alkyl, $X_1$ is $CH_2$ or O, while $X_2$ is O or $C(R_{25})_2$, and each $R_{25}$ may be the same or different and is a hydrogen, a cycloaliphatic group, an aromatic ring, a heteroaromatic ring or a halogen atom, or a heterocarbyl group selected from the groups consisting of $NR_2$, OR and SR, where R is a hydrocarbyl group of $C_1$ to $C_{20}$, or a heterohydrocarbyl group having 1 to 20 atoms, each independently selected from C or a heteroatom, wherein each heteroatom is independently O, S, Si, Ge, P, or N, and may themselves be substituted or unsubstituted as required by the valency of the heteroatom, wherein two $R_{25}$ groups may combine in a fused ring, and Y is a pyrrole group bound via the nitrogen atom to phosphorus, wherein each pyrrole group may bear multiple substituents selected from among the groups alkyl, alkoxy, acyl, carboxyl, carboxylate, cyano, —SO$_3$H, sulfonate, amino, trifluoromethyl and halogen;

wherein the process has a turnover frequency of 0.0118 hr$^{-1}$ or greater.

2. The process of claim 1 in which the transition metal is rhodium.

3. The process of claim 2 in which the alkyl groups of $R_2$-$R_7$ and $R_9$-$R_{24}$ are of 1-20 carbon atoms.

4. The process of claim 3 in which $R_2$-$R_7$ and $R_9$-$R_{24}$ is each independently hydrogen, methyl, ethyl, isopropyl or tort-butyl.

5. The process of claim 2 in which pyrrole group (Y) substituents are carboxylates of 1-6 carbon atoms.

6. The process of claim 5 in which the carboxylate groups are methoxylate or ethoxylate.

7. The process of claim 2 in which the bidentate ligand is selected from the group consisting of:

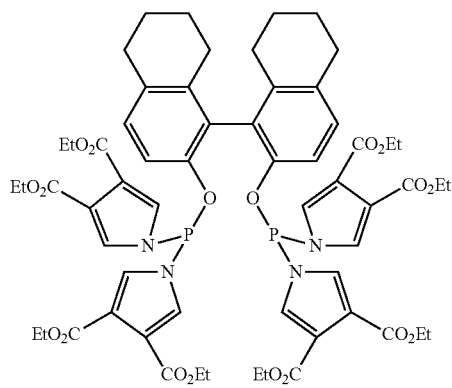

Ligand 1

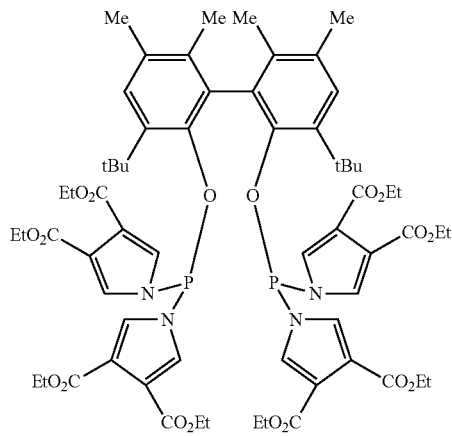

Ligand 2

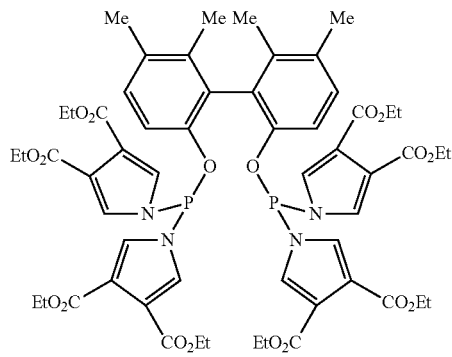

Ligand 3

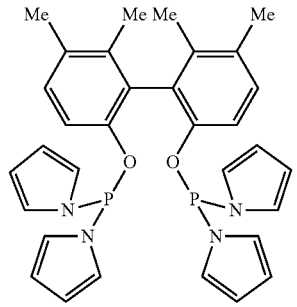

Ligand 4

-continued
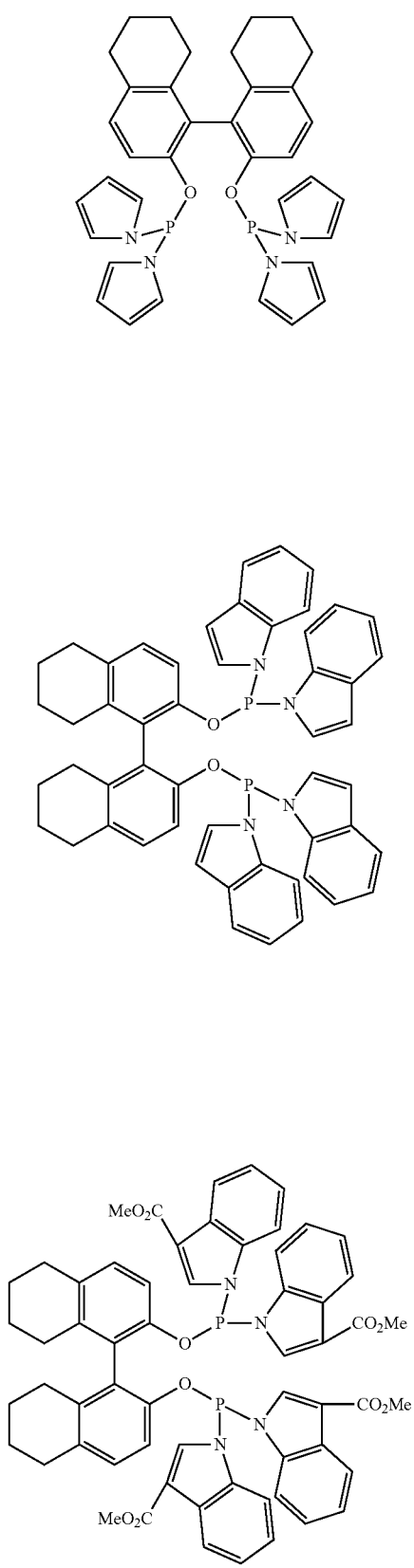
Ligand 6
Ligand 5
Ligand 7
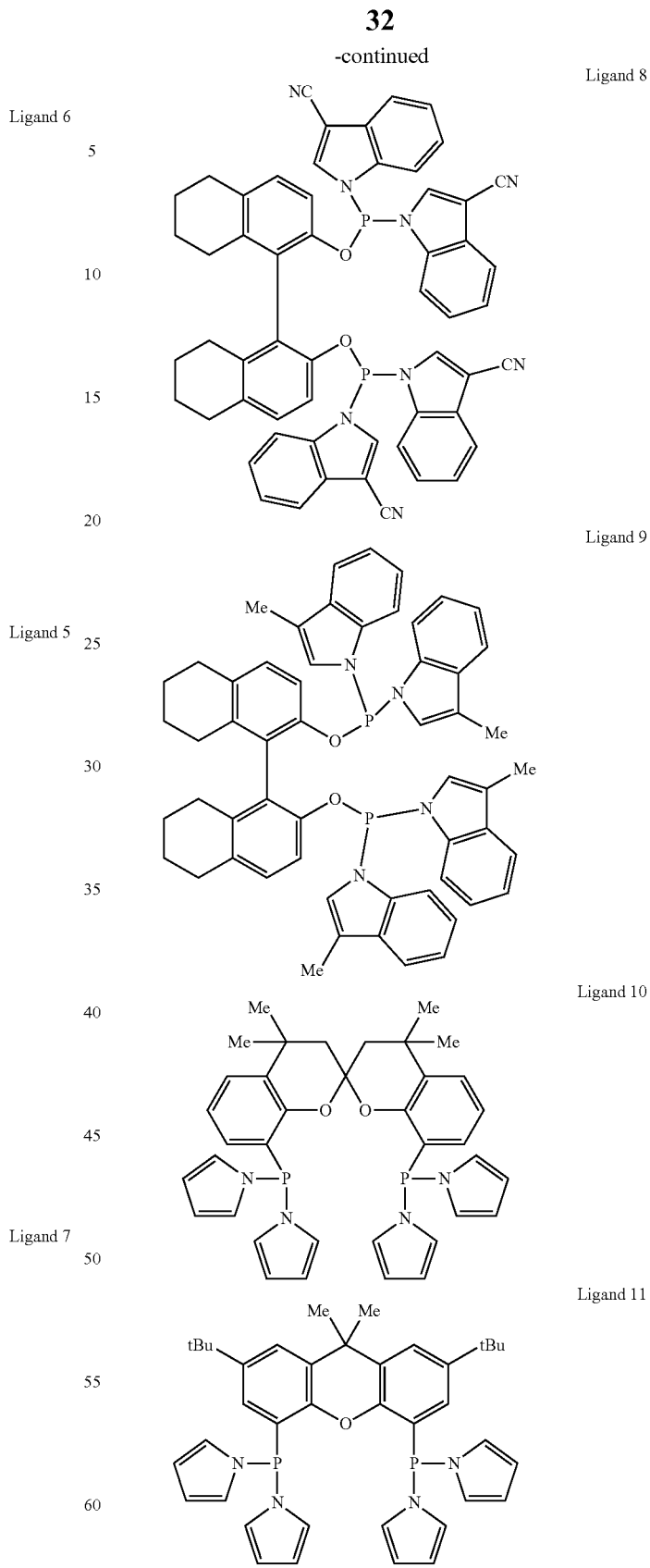
Ligand 8
Ligand 9
Ligand 10
Ligand 11
8. A process for the hydroformylation of ethylene with a rhodium catalyst promoted with a bidentate ligand selected from the group consisting of:

Ligand 1
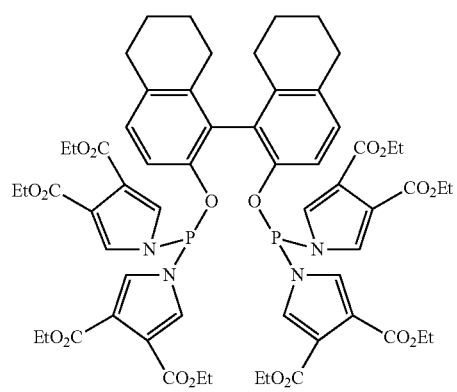
Ligand 2
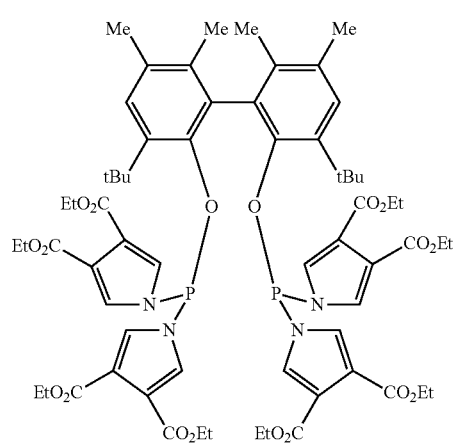
Ligand 3
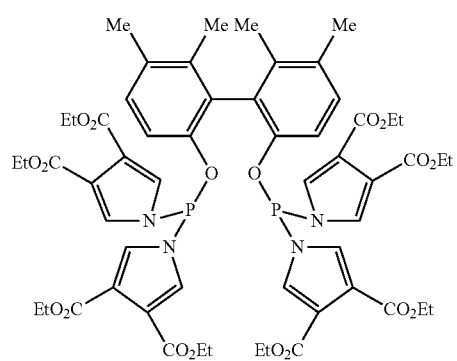
Ligand 4
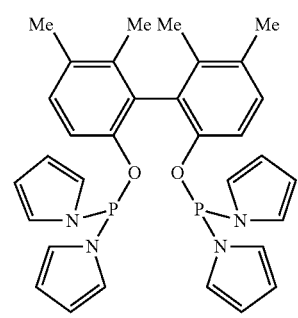
Ligand 6
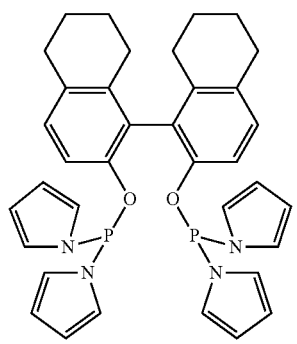
Ligand 5
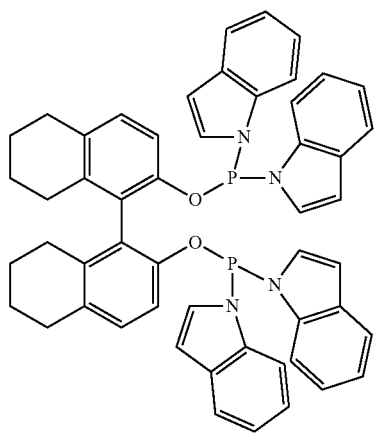
Ligand 7
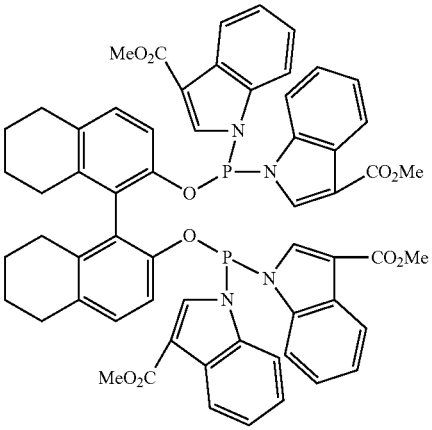

Ligand 8
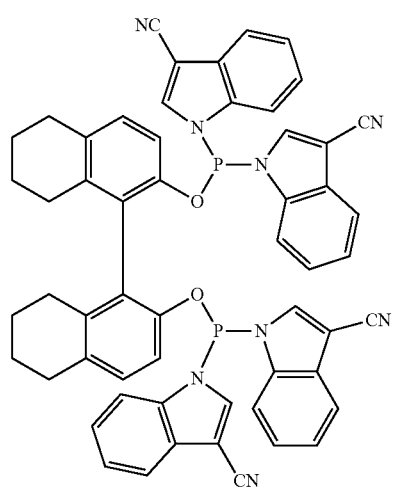
Ligand 9
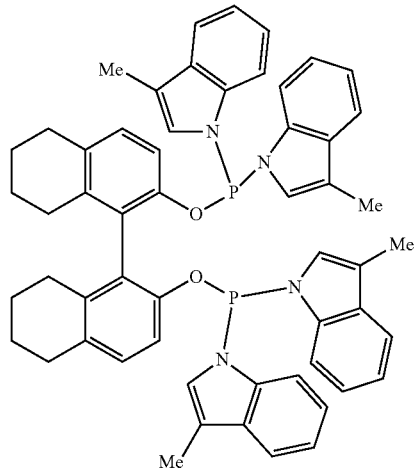
Ligand 10
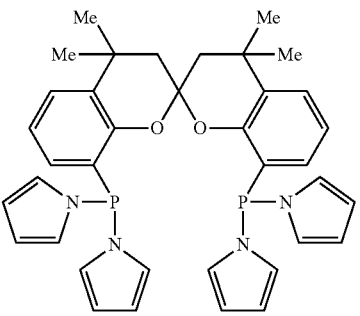
Ligand 11
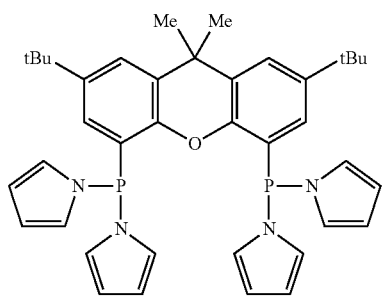
* * * * *